US010016213B2

(12) United States Patent
Kobayashi et al.

(10) Patent No.: US 10,016,213 B2
(45) Date of Patent: Jul. 10, 2018

(54) MANTLE TUBE AND TREATMENT TOOL

(71) Applicant: OLYMPUS CORPORATION, Shibuya-ku, Tokyo (JP)

(72) Inventors: Hiroyoshi Kobayashi, Tokyo (JP); Takami Shibazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 289 days.

(21) Appl. No.: 14/862,945

(22) Filed: Sep. 23, 2015

(65) Prior Publication Data

US 2016/0081714 A1     Mar. 24, 2016

Related U.S. Application Data

(63) Continuation of application No. PCT/JP2014/053303, filed on Feb. 13, 2014.

(Continued)

(51) Int. Cl.
*A61B 17/34*     (2006.01)
*A61B 17/29*     (2006.01)
(Continued)

(52) U.S. Cl.
CPC .... *A61B 17/3417* (2013.01); *A61B 17/00234* (2013.01); *A61B 17/29* (2013.01); *A61B 17/3421* (2013.01); *A61B 17/3423* (2013.01); *A61B 34/70* (2016.02); *A61B 2017/00314* (2013.01); *A61B 2017/00318* (2013.01);
(Continued)

(58) Field of Classification Search
CPC .......... A61B 1/06; A61B 17/00; A61B 17/29; A61B 17/34; A61B 17/3417; A61B 17/3421; A61B 17/00234; A61B 17/3423
See application file for complete search history.

(56) References Cited

U.S. PATENT DOCUMENTS 5,916,147 A    6/1999   Boury
2003/0149338 A1   8/2003   Francois et al.
(Continued)

FOREIGN PATENT DOCUMENTS

JP    2003-530975 A    10/2003
JP    2007-502198 A     2/2007
(Continued)

OTHER PUBLICATIONS

Partial Supplementary European Search Report dated Sep. 29, 2016 received in PCT/JP2014053303.
(Continued)

*Primary Examiner* — Victor Nguyen
(74) *Attorney, Agent, or Firm* — Scully, Scott, Murphy & Presser, P.C.

(57) ABSTRACT

A mantle tube including a bendable member, which is formed in such a way as to be received in an elongate, annular, cylindrical member, includes two fixed sites that are fixed to the cylindrical member and a bendable site that is interposed between these fixed sites and bendable in a direction intersecting a longitudinal direction thereof, an angle adjustment member that is capable of adjusting a bending angle of the bendable site, and an angle holding mechanism that is capable of holding, at any desired bending angle, the bendable site bent by the angle adjustment member.

7 Claims, 27 Drawing Sheets

Related U.S. Application Data

(60) Provisional application No. 61/806,201, filed on Mar. 28, 2013, provisional application No. 61/806,429, filed on Mar. 29, 2013.

(51) Int. Cl.
*A61B 17/00* (2006.01)
*A61B 34/00* (2016.01)
*A61B 90/50* (2016.01)

(52) U.S. Cl.
CPC ............... *A61B 2017/00991* (2013.01); *A61B 2017/2901* (2013.01); *A61B 2017/2906* (2013.01); *A61B 2017/2927* (2013.01); *A61B 2017/3443* (2013.01); *A61B 2090/508* (2016.02)

(56) References Cited

U.S. PATENT DOCUMENTS

| | | |
|---|---|---|
| 2004/0236316 A1 | 11/2004 | Danitz et al. |
| 2004/0263102 A1 | 12/2004 | Kraus et al. |
| 2006/0108958 A1 | 5/2006 | Brenner |
| 2008/0051631 A1* | 2/2008 | Dejima ............... A61B 1/0052 600/114 |
| 2009/0216245 A1 | 8/2009 | Viola |
| 2010/0042077 A1 | 2/2010 | Okada |
| 2011/0245615 A1 | 10/2011 | Iwasaka |
| 2012/0053415 A1 | 3/2012 | Bunch et al. |
| 2012/0190920 A1 | 7/2012 | Hasser et al. |
| 2012/0253131 A1 | 10/2012 | Malkowski et al. |

FOREIGN PATENT DOCUMENTS

| | | |
|---|---|---|
| JP | 2007-527766 A | 10/2007 |
| JP | 4532188 B2 | 8/2010 |
| JP | 2011-212316 A | 10/2011 |
| JP | 2012-100864 A | 5/2012 |
| JP | 2012-143581 A | 8/2012 |
| JP | 2012-152562 A | 8/2012 |
| WO | 2005/094710 A1 | 10/2005 |
| WO | 2007/120353 A2 | 10/2007 |

OTHER PUBLICATIONS

International Search Report dated Apr. 28, 2014 in corresponding International Patent Application No. PCT/JP2014/053303, together with English language translation.

Extended Supplementary European Search Report dated Jan. 18, 2017 in European Patent Application No. 14 77 4326.4.

* cited by examiner

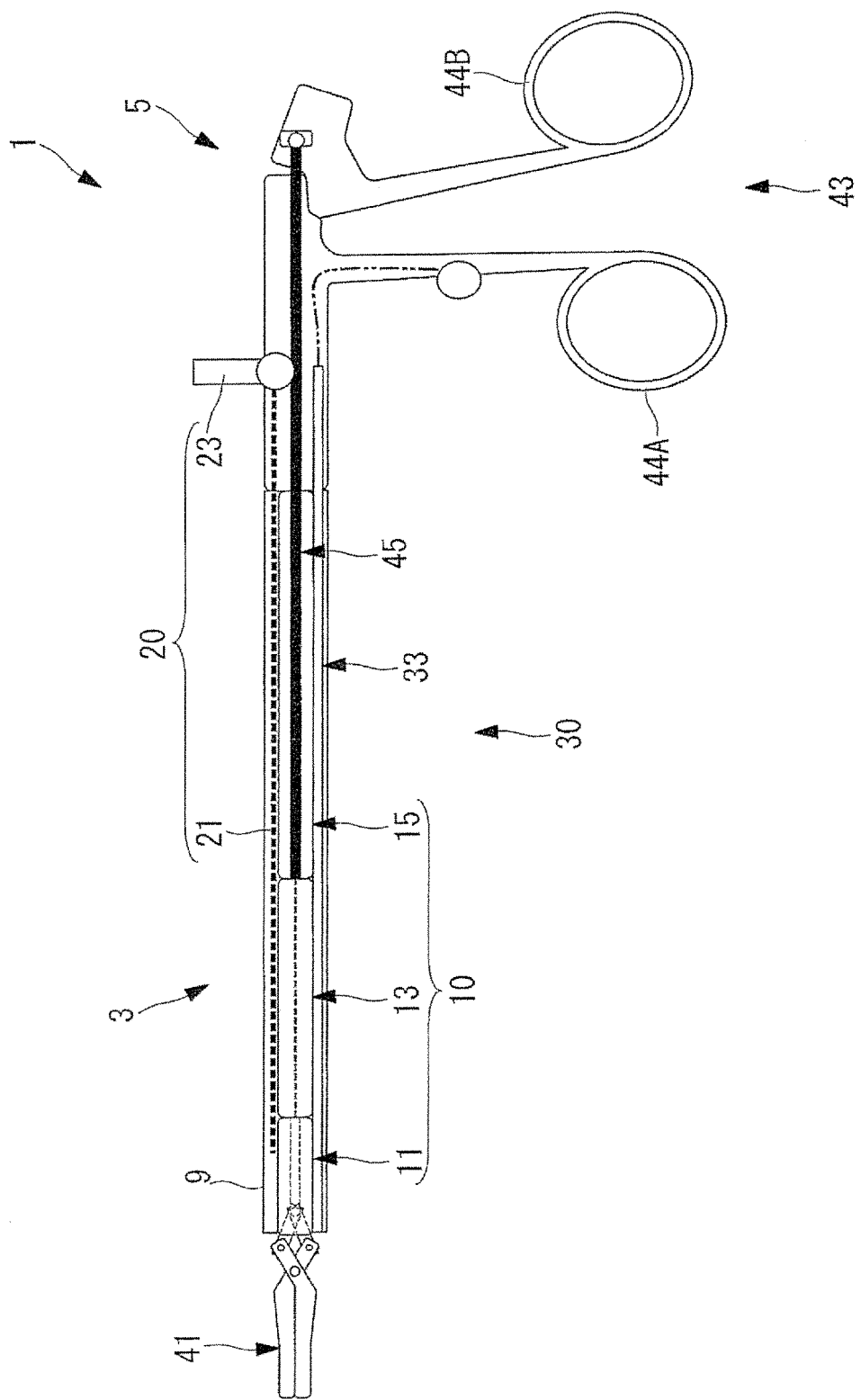

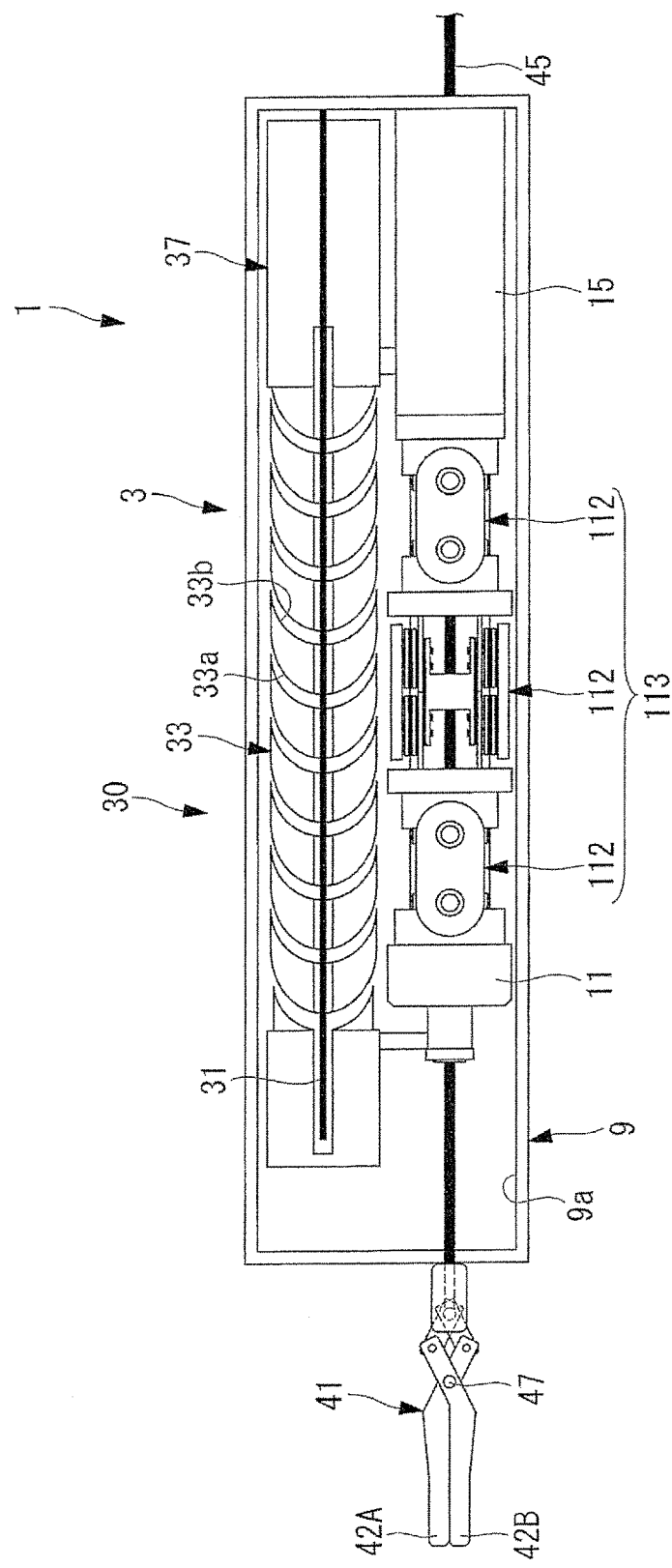

MANTLE TUBE AND TREATMENT TOOL

CROSS-REFERENCE TO RELATED APPLICATIONS

This application is a continuation claiming priority on the basis of U.S. Patent Application No. 61/806,201 provisionally applied in US on Mar. 28, 2013 and U.S. Patent Application No. 61/806,429 provisionally applied in US on Mar. 29, 2013, and based on PCT/JP2014/053303 filed on Feb. 13, 2014. The contents of both the POT application and the U.S. Provisional Application are incorporated herein by reference.

BACKGROUND OF THE INVENTION AND RELATED ART STATEMENT

The present invention relates generally to a mantle tube and a surgical treatment tool (hereinafter called the treatment tool).

So far there has been an intra-corporeal treatment tool used for laparoscopy or the like so as to gain unrestricted access to a site of interest in the body cavity (for instance, see Patent Publications 1 and 2). The intra-corporeal treatment tool described in Patent Publication 1 includes a substantially cylindrical, elongate, flexible wrist that defines an insert unit of an endoscope, and a wire for bending the flexible wrist in its longitudinal direction. According to the intra-corporeal treatment tool of Patent Publication 1, the wire is pulled to bend the flexible wrist thereby allowing the insert unit of the endoscope to gain access to a site of interest in the body cavity.

The intra-corporeal treatment tool described in Patent Publication 2 includes a tubular mantle pipe defining an insertion path for a medical device and a bendable insertion assistant that is inserted through the mantle tube and capable of keeping on maintaining the desired shape. According to the intra-corporeal treatment tool of Patent Publication 2, the bendable insertion assistant inserted into the mantle tube is bent in a constant shape, and the mantle tube is guided following the bent shape of the bendable insertion assistant for forward movement, thereby gaining access to a site of interest in the body cavity while the mantle tube is bent in conformity with the shape of the bendable insert assistant.
[Patent Publication 1] JP(A) 2012-152562
[Patent Publication 2] JP(A) 2011-212316

SUMMARY OF THE INVENTION

In the first aspect of the invention, there is a mantle tube provided which comprises a bendable member that is formed in such a way as to be received in an elongate, annular, cylindrical member and includes two fixed sites that are fixed to the cylindrical member and a bendable site that is interposed between the fixed sites and bendable in a direction intersecting a longitudinal direction thereof, so that the cylindrical member is bent following the bendable site in the direction intersecting a longitudinal direction thereof; an angle adjustment member that is capable of adjusting a bending angle of the bendable site; and an angle holding mechanism that is capable of holding the bendable site bent by the angle adjustment member at any desired bending angle.

BRIEF DESCRIPTION OF THE DRAWINGS

FIG. 3A shows that the mantle tube of FIG. 2 is being linearly extended.

FIG. 4 is schematically illustrative in construction of the mantle tube according to a first modification to the first embodiment of the invention.

DETAILED DESCRIPTION OF PREFERRED EMBODIMENTS

Figure 1:
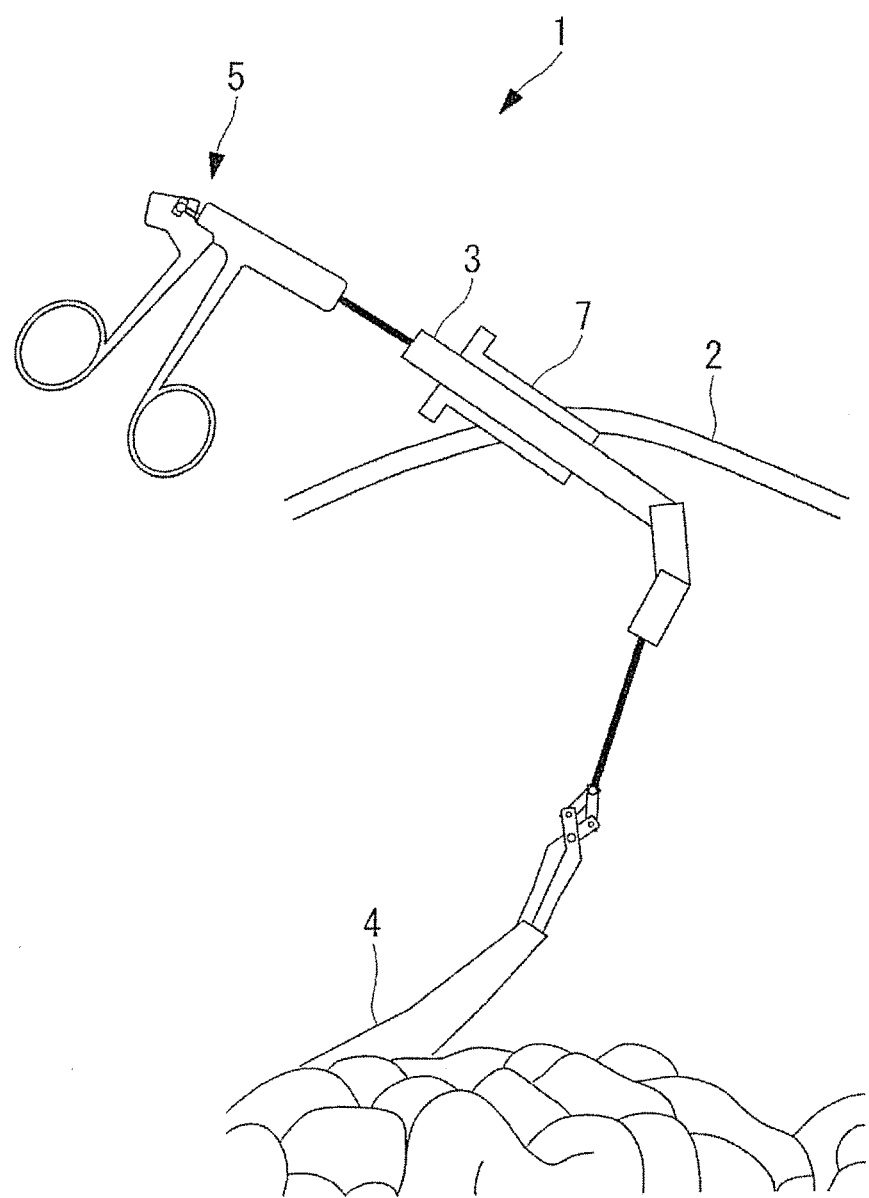
FIG. 1 shows the whole construction of a mantle tube and treatment tool according to the first embodiment of the invention.

The intra-corporeal treatment tool of Patent Publication 1 has some disadvantages: it is required to keep on applying tension to the wire so as to hold the wrist in the bent state, and there is some limitation imposed on the holding force of holding the wrist in its bent state because that holding force depends on the tension of the wire. The intra-corporeal treatment tool of Patent Publication 2 have also some disadvantages: it is not possible to firmly hold the mantle tube in any desired bent shape because the bendable insertion assistant is bent by a pneumatic pressure or other pressure fed from a fluid supply source with the result that the bendable insertion assistant will remain fixed to the predetermined, certain bent shape.

With such situations in mind, the invention has for its object to provide a mantle tube capable of being firmly held in the desired bent shape and a treatment tool including the same.

In the first aspect of the invention, there is a mantle tube provided which comprises a bendable member that is formed in such a way as to be received in an elongate, annular, cylindrical member and includes two fixed sites that are fixed to the cylindrical member and a bendable site that is interposed between the fixed sites and bendable in a direction intersecting a longitudinal direction thereof, so that the cylindrical member is bent following the bendable site in the direction intersecting a longitudinal direction thereof; an angle adjustment member that is capable of adjusting a bending angle of the bendable site; and an angle holding mechanism that is capable of holding the bendable site bent by the angle adjustment member at any desired bending angle.

According to this aspect of the invention, the bendable site of the bendable member is bent by the angle adjustment member, and the bending angle of the bendable site of the bendable member is held by the angle holding member whereby the bent shape of the bendable member is maintained without keeping on applying tension to the bendable member by the angle adjustment member.

Thus, while the bendable member is received or accommodated in the annular, elongate, cylindrical member with the two fixed sites secured to the cylindrical member, the bendable site of the bendable member may be bent by the angle adjustment member whereby the cylindrical member is bent following the bent shape of the bendable member and the bending angle of the bendable site of the bendable member is held by the angle holding mechanism, allowing the bent shape of the cylindrical member to be maintained in place. It is thus easy to firmly hold the cylindrical member in any desired bent shape.

In the aspect, the angle holding mechanism may comprise a flexible wire member that extends along the bendable member and is fixed at one end to a front-end side fixed site of the bendable member, a plurality of interconnected structure-forming members that are arranged along the wire member and capable of coming into contact with one another and spacing away from one another in an arrangement direction thereof, and a pressing member for causing the interconnected structure-forming members to be guided by the wire member so that they are pressed together in such a way as to come close to one another in the arrangement direction, wherein the plurality of interconnected structure-forming members are pressed together by the pressing member in the arrangement direction whereby an interconnected state thereof bent following a bent shape of the bendable member is maintained by friction.

Such an arrangement ensures that the interconnected structure-forming members are pressed together by the pressing member to maintain the interconnected state of the bent shape following the bendable member whereby the bent shape of the bendable member is held by way of the wire member. It is thus possible to simplify the arrangement of taking hold of the bending angle of the bendable site of the bendable member.

In the aspect, the bendable member may include at least two the bendable sites that are capable of bending in mutually different directions, and the angle adjustment member may be capable of angle adjustment for each of the bendable sites.

Such an arrangement ensures that a plurality of bendable sites of the bendable member are bent in their respective directions at their respective bending angles adjusted by the angle adjustment member so that they are held by the angle holding mechanism at their respective bending angles. Therefore, if the bendable member is accommodated or received in the cylindrical member, it is then possible to bend the cylindrical member integrally in the bending direction at the bending angle for each of the bendable sites of the bendable member, thereby taking hold of its bent shape. In other words, the degree of freedom in the bent shape of the cylindrical member may be increased only as many as the bendable sites of the bendable member.

In the aspect, the wire member may be inserted through all of the interconnected structure-forming members in the arrangement direction and fixed to the interconnected structure-forming member at the foremost end, and the pressing member may apply a press to the interconnected structure-forming member at the rearmost end, the press being toward the front end of the arrangement direction.

Such an arrangement ensures that only by allowing the pressing member to press the interconnected structure-forming member at the rearmost end toward the front end, a plurality of interconnected structure-forming members abut against one another in the arrangement direction, resulting in maintenance of the interconnected state of the bent shape in conformity with the bendable member. It is thus possible to easily take hold of the bending angle of the bendable site of the bendable member by means of these interconnected structure-forming members.

In the aspect, the interconnected structure-forming member may include a spherical connecting surface having a mutual correlation between it and an adjoining other interconnected structure-forming member.

Such an arrangement ensures that the area of contact between the interconnected structure-forming members is increased so much so that the interconnected state of the interconnected structure-forming members is maintained in a stable manner. Further, the interconnected structure-forming members may be bent and connected together in any desired direction intersecting the arrangement direction.

In the aspect, the interconnected structure-forming member may include a connecting portion having a mutual correlation to an adjoining other interconnected structure-forming member, and such connecting portions are connected together to impose limitation on the bending of the bendable member in a direction intersecting the bending direction thereof.

Such an arrangement ensures that in an interconnected state of a plurality of interconnected structure-forming members, the bending of the bendable member in a direction intersecting the bending direction thereof is limited thereby to increase resistance to the direction intersecting the bending direction of the bendable member.

In the aspect, the angle holding mechanism may include a resilient member interposed between adjoining ones of the interconnected structure-forming members, the resilient member being capable of absorbing force of contact of the interconnected structure-forming members with each other.

Such an arrangement makes sure close contact of the interconnected structure-forming members with each other so much so that the linkage state of the interconnected structure-forming members is maintained in a more stable manner.

In the aspect, the bendable member may include an insertion path through which the medical device is insertable, and the angle holding mechanism may be located outside of the insertion path of the bendable member.

Such an arrangement ensures that there is a space, the size of the angle holding mechanism, provided in the insertion path taken by the bendable member in contrast with the angle holding mechanism located in the insertion path for the bendable member.

In the second aspect of the invention, there is a treatment tool provided, which comprises a mantle tube as recited in any one of the embodiments, and a medical device insertable into a through-hole in the mantle tube, wherein the medical device includes a treatment member located in such a way as to project out of a front end of the mantle tube for giving treatment to a site of interest, an operating unit located outside of a base end of the mantle tube for operating movement of the treatment member, and a transmission unit for transmitting movement operated by the operating unit to the treatment member.

This aspect of the invention ensures that by using the operating unit located on the base end side of the mantle tube, a gripper member located on the front end side of the mantle tube is operated by way of the transmission unit. Also, with the mantle tube by which the cylindrical member can be firmly held in the desired bent shape, the medical device may be inserted into the body cavity by way of the desired path to locate the gripping member at the desired position. It is thus possible for a surgeon to perform a surgical operation or the like on a patient without applying much burden on the patient.

In the aspect, the mantle tube may be constructed of a plurality of unit sheath tubes in an extendable manner, and the treatment tool may further include an extension variable part located within the mantle tube for adjusting the amount of extension or contraction of the mantle tube.

In the aspect, the treatment tool may further include a pressure-receiving part positioned in a junction between adjoining ones of the unit sheath tubes, and a pressure source for adjusting an amount of a pressure medium contained in the pressure-receiving part.

In the aspect, the pressure-receiving part is fixed to the unit sheath tube positioned at a front end of the mantle tube and to the unit sheath tube positioned at a rear end of the mantle tube, and has a function of the extension variable part.

In the aspect, the extension variable part may include a cylinder fixed to the unit sheath tube on one end side of the mantle tube, a piston fixed to the unit sheath tube on the other end side of the extendable mantle tube, and a pressure source for adjustment of an amount of a pressure medium within the cylinder.

In the aspect, the extension variable part may include an extendable wire-like member fixed to the unit sheath tube positioned at a front end of the mantle tube and wound around a hook mounted on other unit sheath tube, and an extendable wire-like member adjustor component for adjustment of an amount of the extendable wire-like member to be let out.

In the aspect, the extension variable member may include a cam mechanism formed on the unit sheath tube, and a rotatory part to rotate the unit sheath tube.

In the aspect, the treatment tool may include an extension-limiting wire-like member fixed to the unit sheath tube positioned at a front end of the mantle tube for limiting an amount of extension of the mantle tube, and an extension-limiting wire-like member adjusting part for adjustment of an amount of the extension-limiting wire-like member to be let out.

The mantle tubes according to several specific aspects of the invention produce advantages of being firmly held in the desired bent shape, and the treatment tools according to some specific aspects of the invention make it possible to perform surgical treatment on a site of interest in the body cavity by use of the mantle tube.

First Embodiment of the Invention

The mantle tube and treatment tool according to the first embodiment of the invention will now be explained with reference to the accompanying drawings.

As shown typically in FIG. 1, the treatment tool 1 according to this embodiment is inserted into the body of a patient through a trocar 7 punctured in the body wall 2 of the patient such as the abdominal wall to take a grip of an organ 4, etc.

This treatment tool 1 comprises an elongate, tubular mantle tube 3 capable of being inserted into the trocar 7, and a flexible treatment tool (medical device) 5 that is guided by the mantle tube 3 into the body cavity where an operator takes a grip of the organ 4 or the like. The treatment tool 1 is also operable to support the mantle tube 3 by the trocar 7 so that the foremost portion of the flexible treatment tool 5 inserted in the body cavity is movable with the trocar 7 as a fulcrum.

Figure 2:
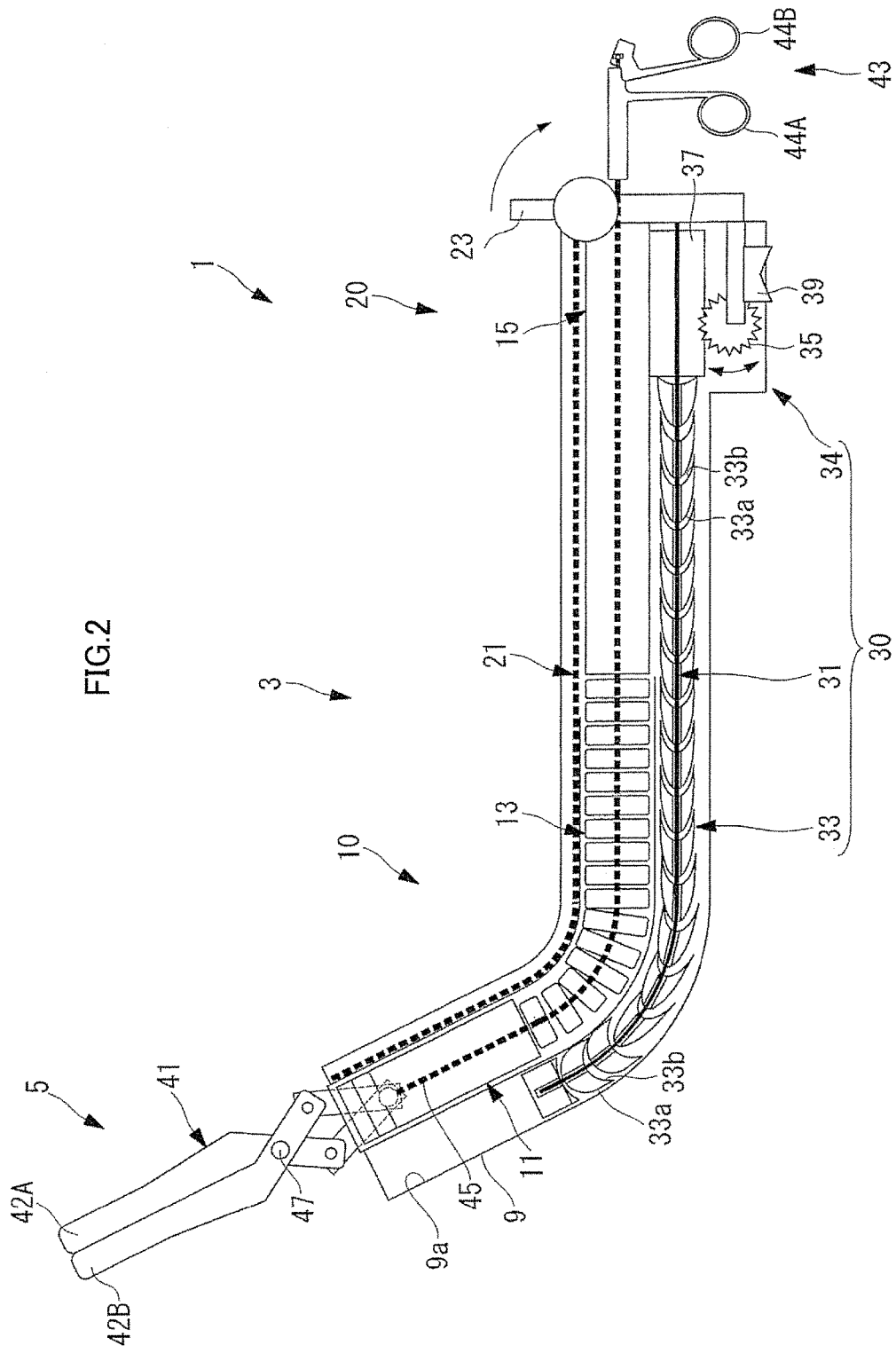
FIG. 2 shows the internal construction of the mantle tube of FIG. 1.

First of all, the construction of the mantle tube 3 is explained. As shown in FIG. 2, the mantle tube 3 comprises an elongate, tubular case (cylindrical member) 9 having a longitudinally extending through-hole 9a, a bendable member 10 that is received in the through-hole 9a in the case 9 to bend the case 9 in a direction intersecting the longitudinal direction, an angle adjustment member 20 capable of adjusting the bending angle of the bendable member 10, and an angle holding mechanism 30 that is capable of holding the bendable member 10 bent by the angle adjustment member 20 at any desired bending angle.

Formed of a flexible material, the case 9 is capable of bending following the bending movement of the bendable member 10 in a direction intersecting the longitudinal direction. The case 9 may also be fitted in the trocar 7.

The bendable member 10 has a length substantially equal to the length of the mantle tube 3. This bendable member 10 comprises, in order from its front end, an elongate front-end frame (fixed site) 11 formed of a hard material and having a substantially cylindrical shape, an elongate coil spring (bendable site) 13 that is connected at one end to the front-end frame 11 and capable of bending in a direction intersecting the longitudinal direction of the case 9, and a substantially cylindrical, elongate rear-end frame (fixed site) 15 that is connected to the other end of the coil spring 13 and formed of a hard material.

Referring to the bendable member 10, for instance, the front-end frame 11, coil spring 13 and rear-end frame 15 get longer in length in this order, and the coil spring 13 is located somewhat nearer to the front end side rather than to the intermediate point of the case 9 in the longitudinal direction. The front-end frame 11 is fixed to the front end of the case 9, and the rear-end frame 15 is fixed to the base end of the case 9. The coil spring 13 is supported by the front-end frame 11 and rear-end frame 15 in such a way as to be bendable within the case 9 in a direction intersecting the longitudinal direction.

The front-end frame 11, coil spring 13 and rear-end frame 15 have a hollow structure (insertion path) where they communicate with one another along the longitudinal direction of the case 9, so that the foremost end of the flexible surgical device 5 inserted from one end of the case 9 into the through-hole 9a can pass through the front-end frame 11, coil spring 13 and rear-end frame 15, going out of, or going back in, the other end of the case 9.

The angle adjustment member 20 comprises a flexible bending wire 21 that allows for bending movement of the coil spring 13, and an operating lever 23 capable of selection of the bending angle of the coil spring 13. The bending wire 21 is connected at one end to the front-end frame 11 of the bendable member 10 and at the other end to the operating lever 23.

The operating lever 23 is fixed to the base end of the rear-end frame 15 of the bendable member 10. This operating lever 23 is tilted or inclined so stepwise that the bendable member 10 can be pulled toward the base end for stepwise bending of the coil spring 13 depending on the tilt angle of the operating lever 23.

Figure 3B:
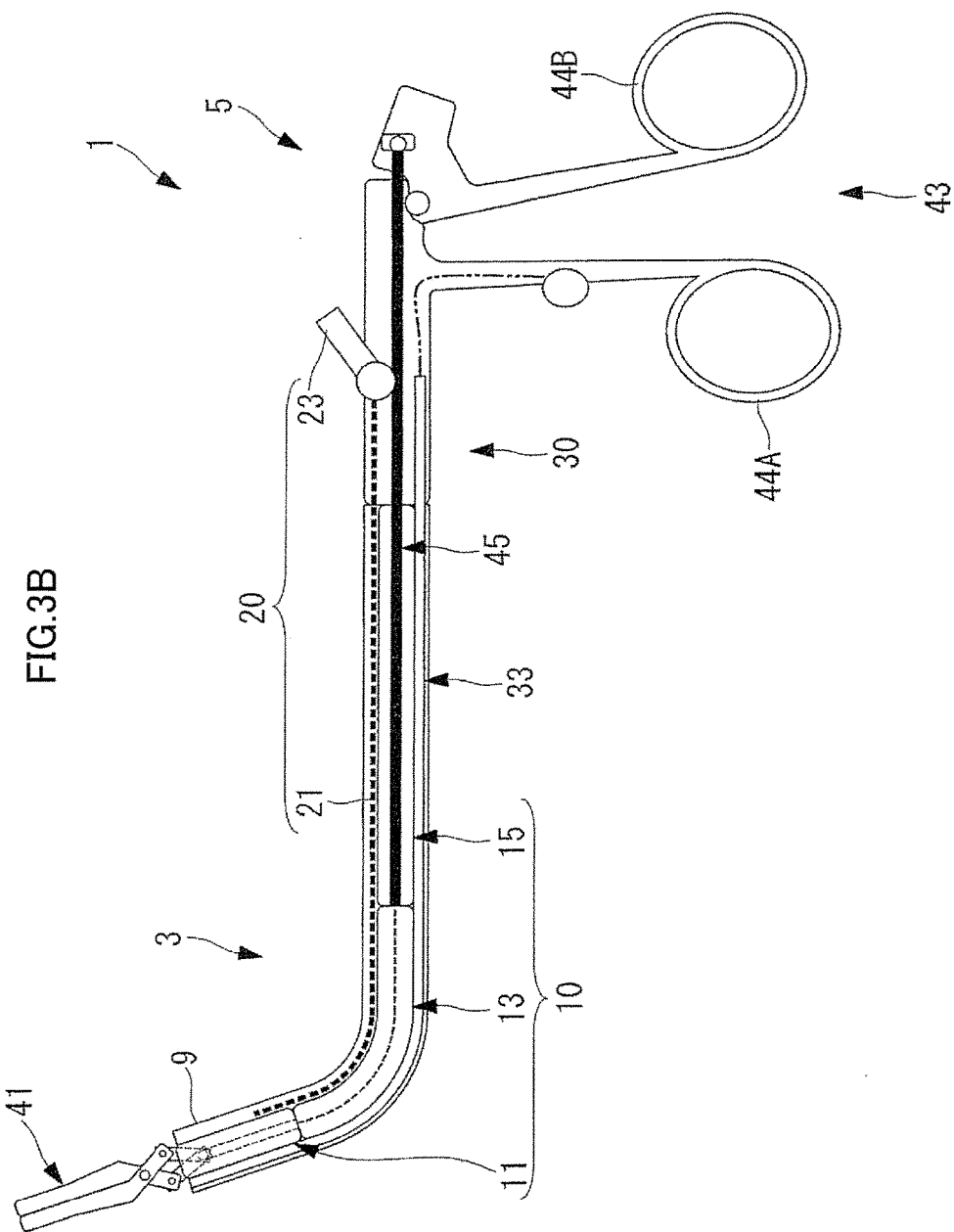
FIG. 3B shows that the mantle tube of FIG. 3A is being bent.

As shown typically in FIG. 3A, as the operating lever 23 is kept upright, it causes the bending wire 21 to go forward, placing the coil spring 13 in a linearly extended state. As shown in FIG. 3B, on the other hand, stepwise inclination of the operating lever 23 causes the bending wire 21 to be slowly pulled toward the base end of the case 9, so that the coil spring 13 can bend stepwise in the direction intersecting the longitudinal direction at an angle corresponding to the tilt angle of the operating lever 23.

The angle holding mechanism 30 comprises a flexible holding wire (wire member) 31 that extends along the bendable member 10, a plurality of interconnected structure-forming members 33 that are arranged along the holding wire 31 and capable of contacting one another or spacing away from one another in the arrangement direction, and a pressing mechanism (pressing member) 34 that guides the interconnected structure-forming members 33 by the holding wire 31 to press them close to each other along the arrangement direction.

The holding wire 31 is located outside of the bendable member 10, and fixed at one end to the foremost interconnected structure-forming member 33 and at the other end to the base end of the case 9.

The interconnected structure-forming members 33 run from some midpoint in the longitudinal direction of the front-end frame 11 of the bendable member 10 to some midpoint in the longitudinal direction of the rear-end frame 15 with the coil spring 13 in between. The foremost interconnected structure-forming member 33 is fixed to the front-end frame 11 of the bendable member 10.

Such interconnected structure-forming members 33 are each in a substantially bowl shape, and adjoining interconnected structure-forming members 33 have spherical, correlating connecting surfaces 33a and 33b. For instance, the connecting surface 33a facing the front end side of the case 9 has a convex, spherical shape, whereas the connecting surface 33b facing the base end side of the case 9 has a concave, spherical shape. And the adjoining interconnected structure-forming members 33 are formed such that the connecting surfaces 33a and 33b are in close contact with each other. Each interconnected structure-forming member 33 has a holding wire 31 passage hole (not shown) at a substantially center position of the connecting surface 33a, 33b.

Each interconnected structure-forming member 33 can be guided by the holding wire 31 for movement in the arrangement direction. And these interconnected structure-forming members 33 are pressed together by the pressing mechanism 34 and brought in close contact with each other so that the shape of the interconnected state can be maintained by friction.

Therefore, these interconnected structure-forming members 33 are bendable in the direction intersecting the arrangement direction while they are spaced away from one another, and while they are in close contact with one another, the shape of the interconnected state is kept invariable.

The pressing mechanism 34 comprises a gear 35 having teeth in the peripheral direction, a cylindrical or prismatic pressing frame 37 having teeth mating with the teeth of the gear 35, and a pressing switch 39 for making selection of the rotational direction of the gear 35 as well as the rotation and stop of the gear 35.

The gear 35 is located in such a way as to be rotatable about a rotary shaft (not shown) that extends in a direction orthogonal to the longitudinal direction of the case 9. The pressing frame 37 is located at the rearmost ends of a plurality of interconnected structure-forming members 33, and has a holding wire 31 passage hole (not shown). This pressing frame 37 can be guided by the holding wire 31 depending on the rotation of the gear 35 in such a way as to move in the longitudinal direction of the case 9.

Referring to the pressing mechanism 34, as the pressing frame 37 is moved toward the front end side of the case 9 by rotation of the gear 35 of the pressing mechanism 34, it causes a pressing force to be applied to the rearmost-end interconnected structure-forming member 33 so that all the interconnected structure-forming members 33 can come close to one another. As the pressing frame 37 is moved toward the base end side of the case 9 by reverse rotation of the gear 35 of the pressing mechanism 34, it causes a release of the pressing force so that all the interconnected structure-forming members 33 can be spaced away from one another.

Then, the construction of the flexible treatment tool 5 is now explained. As shown in FIG. 2, this flexible treatment tool 5 comprises a forceps unit (treatment member) 41 for taking a grip of the organ 4, etc. of a patient, an operating unit 43 that enables an operator to grip and operate the forceps unit 41, and a transmitting wire (transmitting unit) 45 for transmitting operation by the operating unit 43 to the forceps unit 41.

The forceps unit 41 is inserted or de-inserted in the mantle tube 3 through the interior of the bendable member 10. FIG. 2 shows that the forceps unit 41 is projecting out of the front-end side of the mantle tube 3. This forceps unit 41 includes a pair of gripping pieces (gripping members) 42A, 42B capable of rocking about a rockshaft 47 extending in the direction intersecting the longitudinal direction.

A pair of gripping pieces 42A, 42B are connected at the base ends with a transmitting wire 45 so that they rocks, with the rockshaft 47 as a fulcrum, through the operation of the operating unit 43 transmitted via the transmitting wire 45 for opening or closing of their front-ends.

The operating unit 43 is located outside of the base end of the mantle tube 3. The operating unit 43 comprises a fixed handle 44A, and a movable handle 44B capable of rocking with respect to the fixed handle 44A, with a pin (not shown) as center. The movable handle 44B is fixedly provided with the other end of the transmitting wire 45.

As the operator takes a grip of the fixed handle 44A and movable handle 44B of the operating unit 43, it causes the movable handle 44B to come close to the fixed handle 44A whereby the transmitting wire 45 is pulled toward the base end side, resulting in closure of the gripping pieces 42A and 42B. As the operator lets go both the handles 44A and 44B, on the other hand, it causes the transmitting wire 45 to move forward, resulting in opening of the gripping pieces 42A and 42B.

The operation of the thus constructed mantle tube 3 and treatment tool 1 is explained.

Referring to the mantle tube 3 and treatment tool 1 according to this embodiment, with the angle holding mechanism 30 not being in operation, a plurality of interconnected structure-forming members 33 are spaced away from one another in the arrangement direction so that they are bendably supported by the holding wire 31, making the case 9 bendable following bending movement of the coil spring 13.

Therefore, as the operator keeps the operating lever 23 upright as shown in FIG. 3A, it causes the bending wire 21 to move forward so that the coil spring 13 extends linearly, so does the case 9 too. As the operator tilts the operating lever 23 as shown in FIG. 3B, on the other hand, it causes the bending wire 21 to be pulled toward the base end side of the bendable member 10 so that the coil spring 13 is bent in the direction intersecting the longitudinal direction, and the case 9 can be bent, too, following the bending angle of the coil spring 13.

Then, actuation of the angle holding mechanism 30 causes the shape of the bendable member 10 to be so held that the shape of the case 9 is held. Specifically, as the gear 35 is rotated to move the pressing frame 37 toward the front end side of the case 9, it allows all the interconnected structure-forming members 33 to come close to one another along the arrangement direction while they are guided by the holding wire 31.

And the adjoining interconnected structure-forming members 33 are in contact with each other, and their connecting surfaces 33b and 33a are in close contact with each other so that the interconnected state of the interconnected structure-forming members 33 connected together in the shape following the shape of the bendable member 10 is maintained by friction between the connecting surfaces 33a and 33b.

Therefore, if the angle holding member 30 is actuated while the coil spring 13 extends linearly as shown in FIG. 3A, it is then possible to maintain the shape of the case 9 such that it extends linearly in the longitudinal direction. On the other hand, if the angle holding mechanism 30 is actuated while the coil spring 13 is bent, as shown in FIG. 3B, it is then possible to maintain the shape of the case 9 such that it bends following the bending angle of the coil spring 13.

In this case, each interconnected structure-forming member 33 has the spherical connecting surfaces 33a and 33b having a mutual correlation to an adjoining other interconnected structure-forming member 33 so much so that the area of contact between the interconnected structure-forming members 33 can be made large, resulting in stable maintenance of the interconnected state of the interconnected structure-forming members 33. These interconnected structure-forming members 33 may be connected together in any direction intersecting the arrangement direction, ensuring that the mantle tube 3 is firmly held in the desired bent shape in the body cavity.

Referring to how the mantle tube 3 and treatment tool 1 are used to take a grip of the organ 4, etc. in the body cavity of a patient, the mantle tube 3 is first inserted in the body cavity by way of the trocar 7 punctured into the body wall 2 such as the abdominal wall of the patient while the flexible treatment tool 5 is removed from the mantle tube 3. Then, the mantle tube 3 is allowed to come close to the organ 4 of interest, etc. while it is bent in conformity with the inside shape of the body cavity. Then, the front end of the mantle tube 3 is placed in opposition to the organ 4 of interest, etc. while the shape of the case 9 is firmly held by the angle holding mechanism 30.

Then, the forceps unit 41 of the flexible treatment tool 5 is inserted from the base end side of the mantle tube 3 into the bendable member 10 and projected out of the front end of the mantle tube 3. This ensures that the forceps unit 41 is guided by the mantle tube 3 to near the organ 4 of interest, etc. In this state, the operator may manipulate the operating unit 43 to open or close the gripping pieces 42A and 42B for the purpose of taking a grip of the organ 4 or the like.

As described above, the mantle tube 3 and treatment tool 1 according to this embodiment of the invention ensures that the bent shape of the case 9 is maintained with no need for keeping on applying tension to the coil spring 13 by the angle adjustment member 20. Therefore, the desired bent shape of the mantle tube 3 can easily be firmly held in the body cavity, making it possible for the flexible treatment tool 5 to take a grip of the organ 4 while burdens on the patient are much relieved.

Provision of the angle holding mechanism 30 outside of the bendable member 10 makes sure there is a space as large as the angle holding mechanism 30 provided within the bendable member 10 in contrast to provision of the angle holding mechanism within the bendable member 10. This allows for easy insertion of the forceps unit 41 in the bendable member 10 and a smooth guidance of the flexible treatment tool 5 by the mantle tube 3.

This embodiment of the invention may be modified or altered as follows.

While the embodiment of the invention has been explained with reference to an example that uses the coil spring 13 for the bendable site of the bendable member 10, it is to be understood that in the first modification, a block or link structure may be used for the bendable site of the bendable member 10.

Referring to a specific example using a bendable site having a link structure, use may be made of a link (bendable site) 113 that includes a plurality of link members 112 and is capable of bending in a direction intersecting the longitudinal direction of the case 9, as is the case with a bendable member 110 shown typically in FIG. 4. In this modification, there are multiple bending wires 21 used, each connected to each link member 112. Bending movement may take place for each link member 112 by way of its associated bending wire 21.

Figure 5:
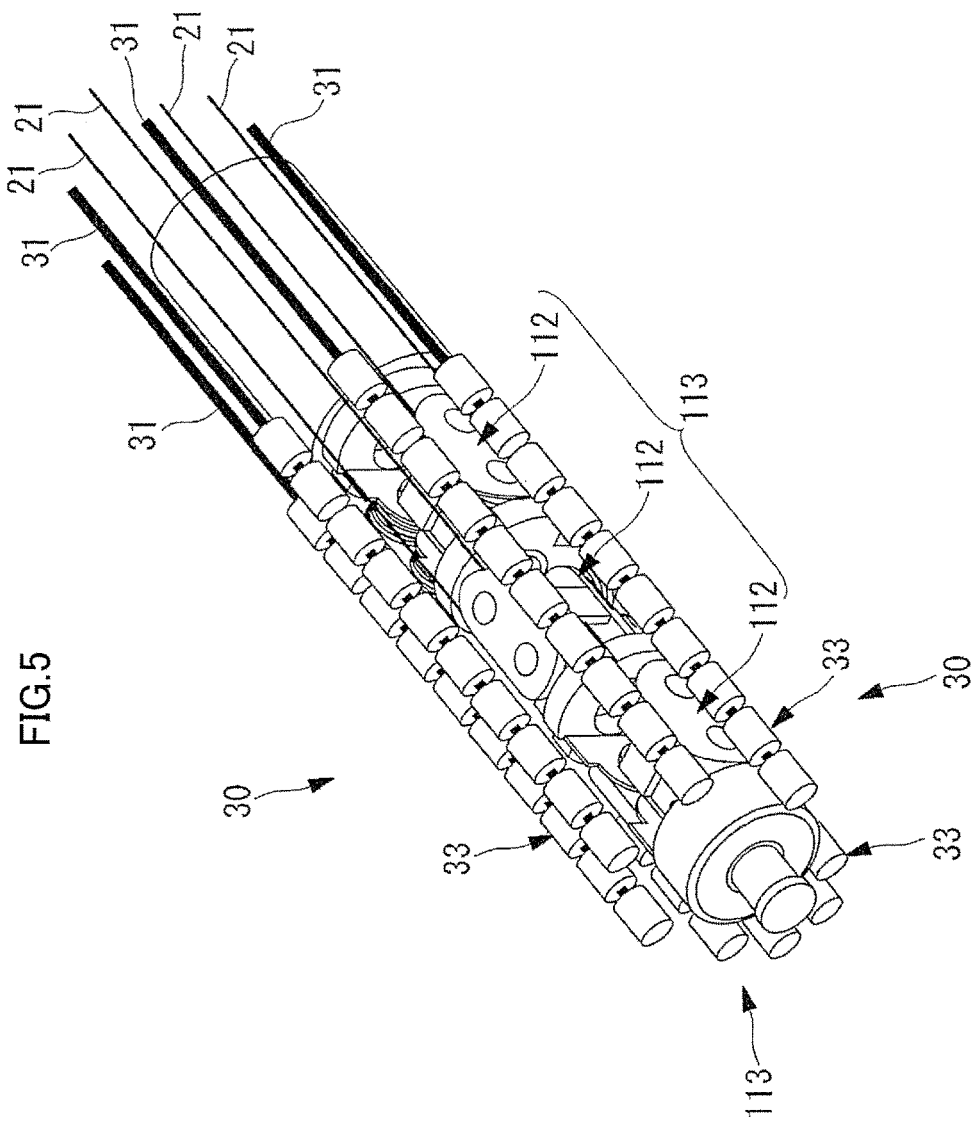
FIG. 5 is schematically illustrative in construction of the holding mechanism, inclusive of portions surrounding it, according to the first modification to the first embodiment of the invention.

In this modification, there are multiple angle holding mechanisms 30 used as shown in FIG. 5. The bending angle may be individually held by each angle holding mechanism 30 for each joint between the link members 112.

Figure 6:
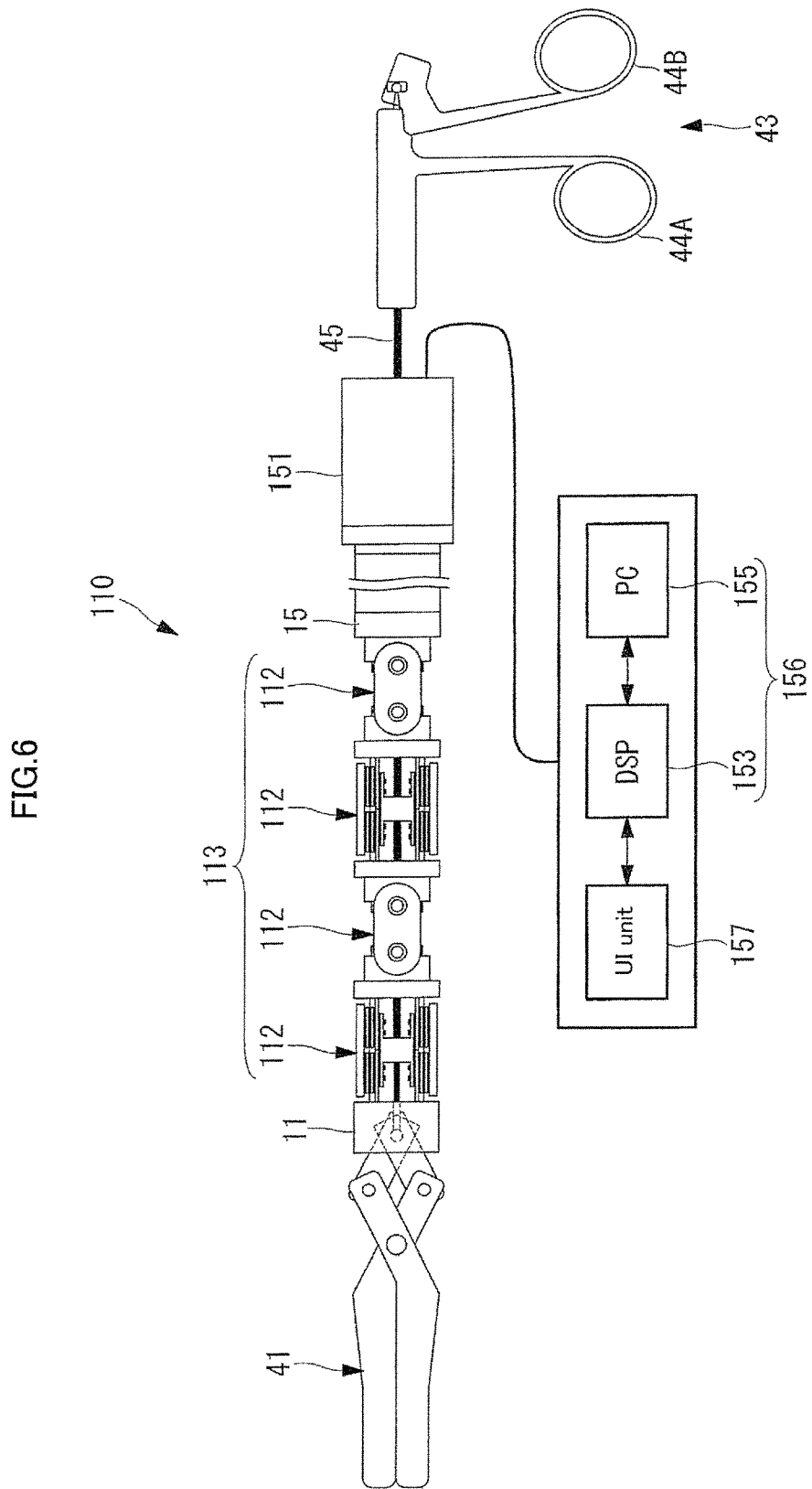
FIG. 6 is schematically illustrative of the mantle tube and treatment tool according to the first modification to the first embodiment of the invention.

In this modification, the mantle tube 3 may include a motor 151 for bending the link 113 of the bendable member 10, as shown in FIG. 6. The motor 151 is connected with a control unit 156 including a DSP (digital signal processor) 153 and a PC (personal computer) 155 for controlling the drive of the motor 151, and a UI (user interface) unit 157 for operation by an operator to control the motor 151 by the control unit 156 so that the operator may perform any desired operation via the UI unit 157.

In this modification, too, the case 9 may be bent by the bendable member 110 as is the case with the embodiment of the invention, and the angle of the link 113 of the bendable member 110 may be held by the angle holding mechanisms 30 to firmly hold the shape of the case 9. The same would hold for a modification having a block structure for the bendable site of the bendable member 110.

Figure 7A:
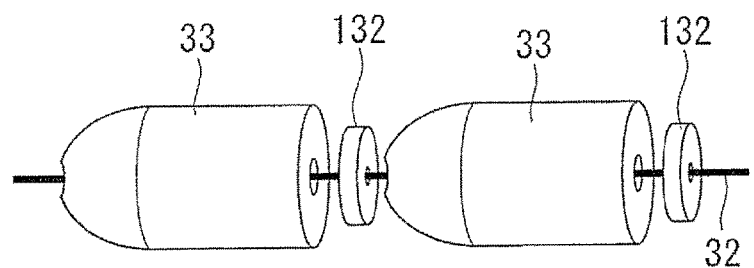
FIG. 7A is schematically illustrative of interconnected structure-forming members according to a second modification to the first embodiment of the invention.

While the adjoining interconnected structure-forming members 33 are in direct contact with each other in the embodiment of the invention as described above, it is to be understood that in the second modification as shown typically in FIG. 7A, the angle holding mechanism 30 may include between the adjoining interconnected structure-forming members 33 a resilient member 132 capable of absorbing force of contact between them.

For instance, the resilient member 132 may be formed of a thin disc form of resin material.

Figure 7B:
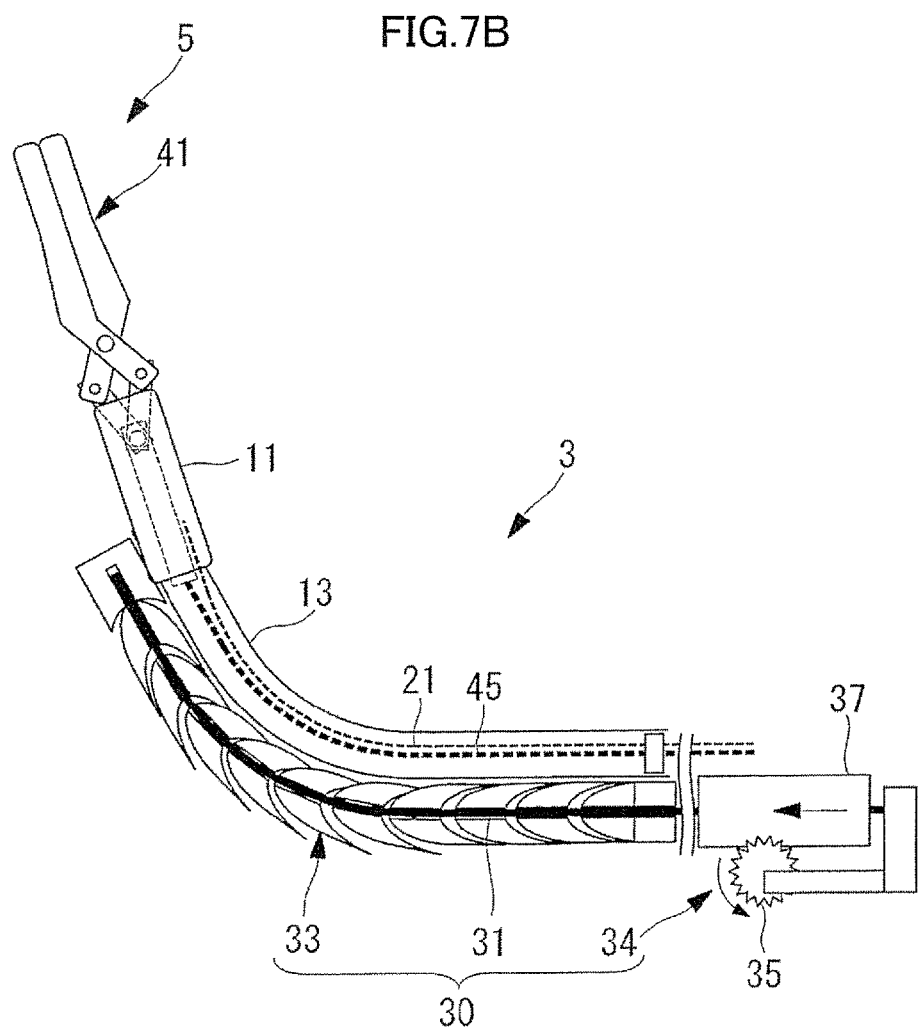
FIG. 7B is illustrative of the mantle tube according to the second modification to the first embodiment of the invention in a bent state.
Figure 7C:
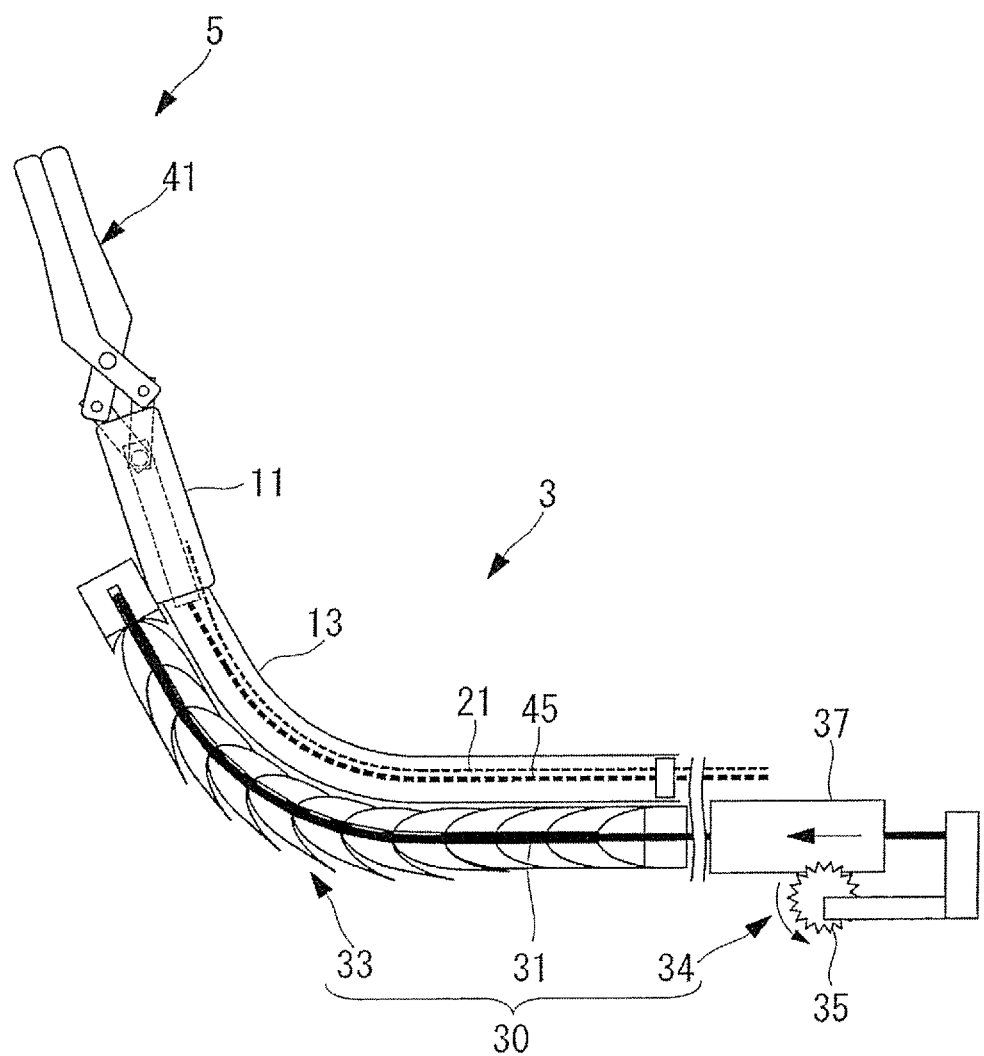
FIG. 7C shows that the mantle tube of FIG. 7B is firmly held in a bent state.

As shown in FIGS. 7B and 7C, this ensures that when the interconnected structure-forming members 33 are in close contact with one another, there are improvements made in such close contact by the pressing mechanism 34, resulting in more stable maintenance of the interconnected state of such interconnected structure-forming members 33. Note here that the resilient member 132 is left out of FIGS. 7B and 7C for the sake of a clearer illustration of the interconnected state of the interconnected structure-forming members 33.

Figure 8A:
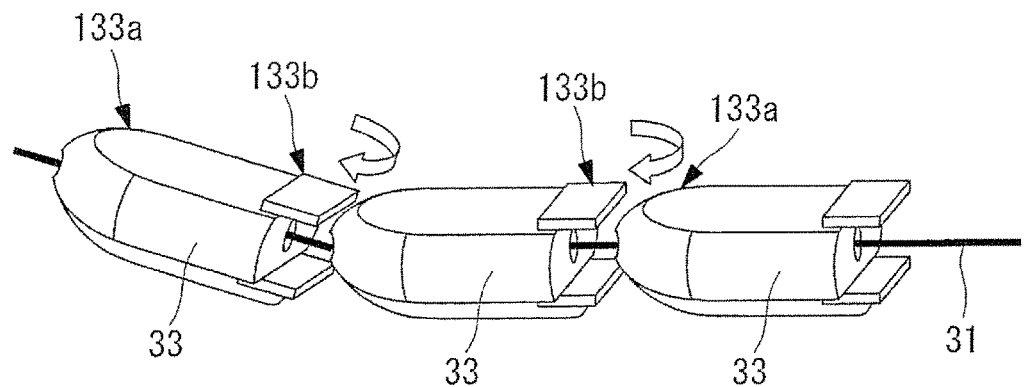
FIG. 8A is schematically illustrative in construction of interconnected structure-forming members according to a third modification to the first embodiment of the invention.

While the interconnected structure-forming members 33 have spherical connecting surfaces 33a and 33b in the embodiment of the invention as described above, it is to be noted that in the third modification, a certain interconnected structure-forming member 33 may have connecting portions 133a and 133b having a correlation to an adjoining interconnected structure-forming member 33 instead of such spherical connecting surfaces 33a and 33b, as shown in FIG. 8A. As these connecting portions 133a and 133b are connected together, it may impose limitation on bending in a direction intersecting the bending direction of the bendable member 10.

In FIG. 8A, the connecting portion 133a defines an R-shaped front end of the interconnected structure-forming member 33, and the connecting portion 133b comprises a pair of protrusions that are located at the base end of the interconnected structure-forming member 33 at a given interval in the widthwise direction and protrude rearward in parallel with each other so that the connecting portion 133a is sandwiched and fitted between the protrusions of the connecting portion 133b in the widthwise direction. This will impose limitation on bending in a direction of sandwiching the connecting portion 133a between the protrusions of the connecting portion 133b.

Figure 8B:
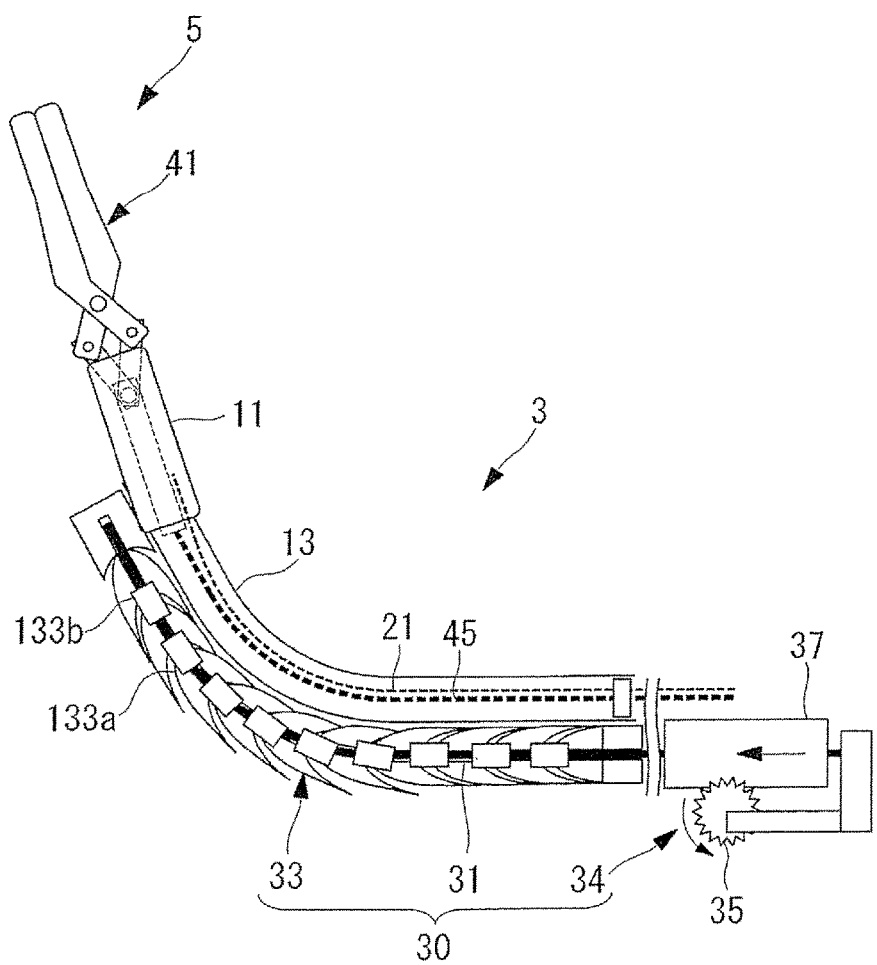
FIG. 8B shows that the mantle tube according to the third modification to the first embodiment of the invention is in a bent state.
Figure 8C:
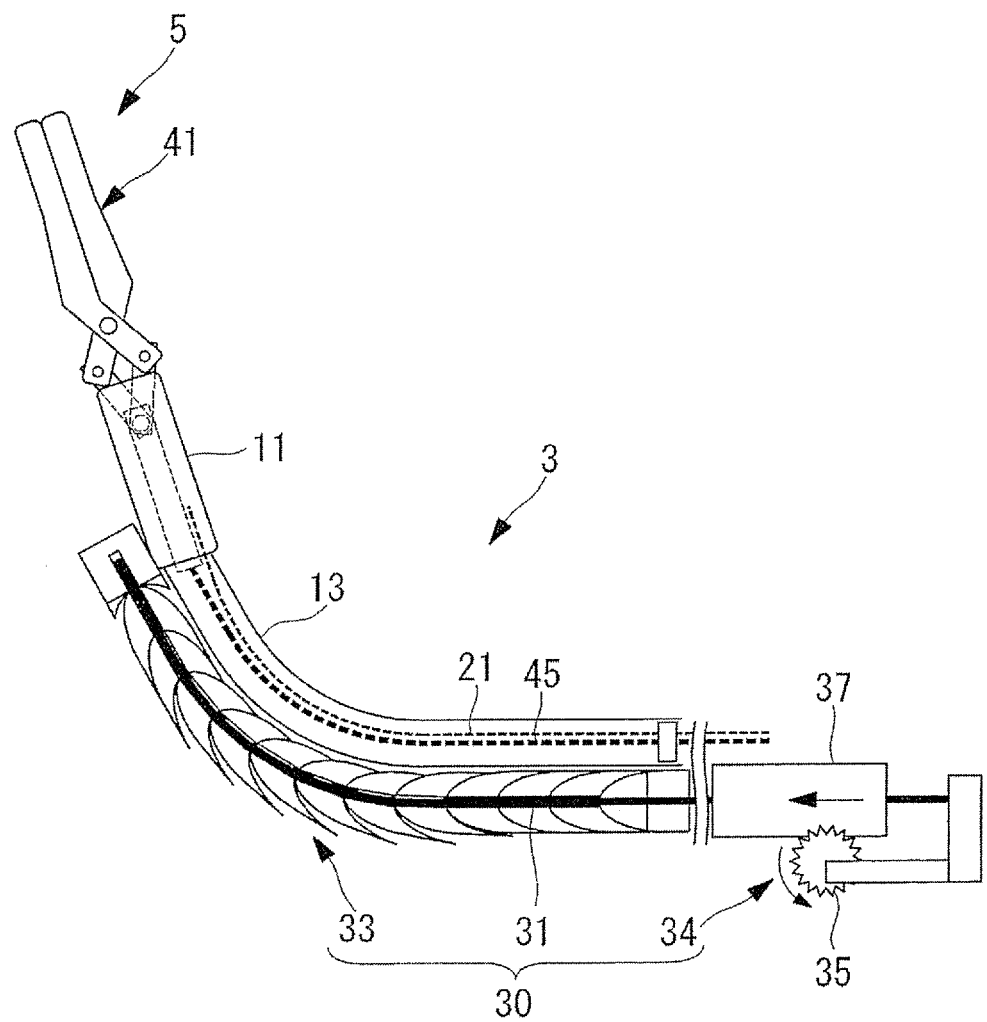
FIG. 8C shows that the mantle tube of FIG. 8B is firmly held in a bent state.

As shown in FIGS. 8B and 8C, this ensures that where a plurality of interconnected structure-forming members 33 are connected together, the connecting portions 133a and 133b impose limitation on the bending of the bendable member 10 in the direction intersecting the bending direction of the bendable member 10, resulting in increased resistance to the direction intersecting the bending direction of the bendable member 10. Note here that to provide a clearer illustration of the interconnected state of the interconnected structure-forming members 33, the connecting portion 133b is left out of FIG. 8C.

Second Embodiment of the Invention

The mantle tube and treatment tool according to the second embodiment of the invention will now be explained.

Figure 9:
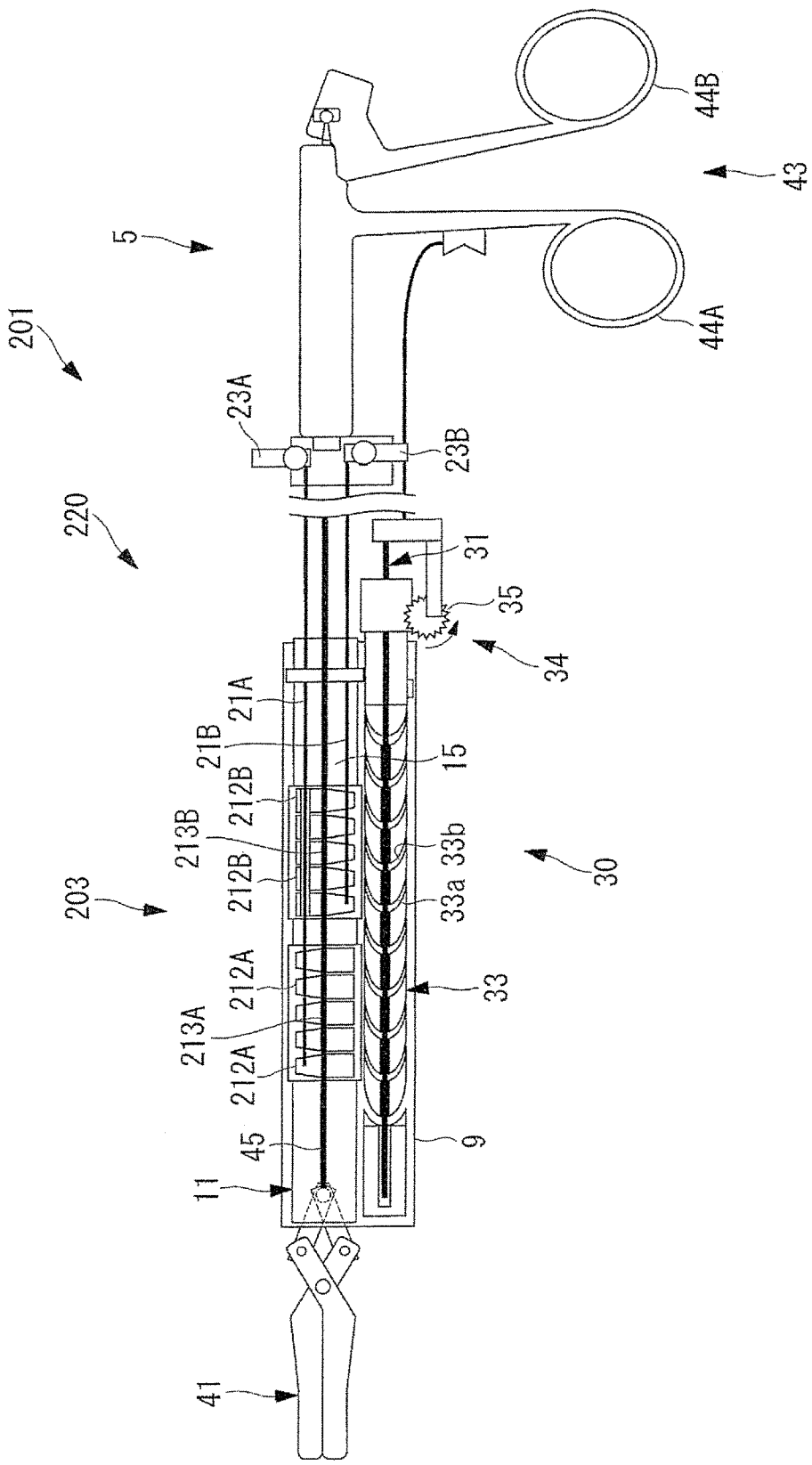
FIG. 9 is illustrative of the whole construction of the mantle tube and treatment tool according to the second embodiment of the invention.

As shown in FIG. 9, the mantle tube 203 and treatment tool 201 according to the instant embodiment are different from those of the first embodiment of the invention in that the bendable member 210 includes bendable sites 213A and 213B having a block structure, which sites are bendable in mutually different directions. Common elements to the mantle tube 3 and treatment tool 1 according to the first embodiment of the invention are indicated by the same reference numerals, so they will not be explained any more.

The bendable member 210 comprises, in order from its front end, a front-end frame 11, a bendable site 213A including a plurality of block members 212A that are arranged in one direction intersecting the longitudinal direction of the case 9 in such a way as to be bendable, a bendable site 213B including a plurality of block members 212B that are arranged in a direction opposite to the bendable site 213A in such a way as to be bendable, and a rear-end frame 15.

The angle adjustment member 220 includes a flexible bending wire 21A for allowing for bending movement of the bendable site 213A, a flexible bending wire 21B for allowing for bending movement of the bendable site 213B, an operating lever 23A for making selection of the bending angle of the bendable site 213A, and an operating lever 23B allowing for making selection of the bending angle of the bendable site 213B.

The bending wire 21A, 21B is connected at one end to block members 212A, 212B arranged at the foremost end, and at the other end to the operating levers 23A and 23B, respectively.

As the operating levers 23A and 23B tilt, it causes the bending wires 21A and 21B to be pulled toward the base end side of the case 9 and the bendable sites 213A and 213B to be bent at angles corresponding to the respective tilt angles.

How the thus assembled mantle tube 203 and treatment tool 201 operate will now be explained.

Referring to the operation of the mantle tube 203 and treatment tool 201 according to this embodiment of the invention, as the operating lever 23A tilts with the angle holding mechanism 30 being not in operation, it causes the bendable site 213A to be bent in one direction intersecting the longitudinal direction, and as the operating lever 23B tilts, it causes the bendable site 213B to be bent in a direction opposite to the bending direction of the bendable site 213A. In other words, as the operating levers 23A and 23B tilt, respectively, it causes the bendable member 10 to be bent in an S-shaped pattern, and the case 9, too, to be bent in an S-shaped pattern in conformity with the bent shape of the bendable sites 213A and 213B.

Figure 10:
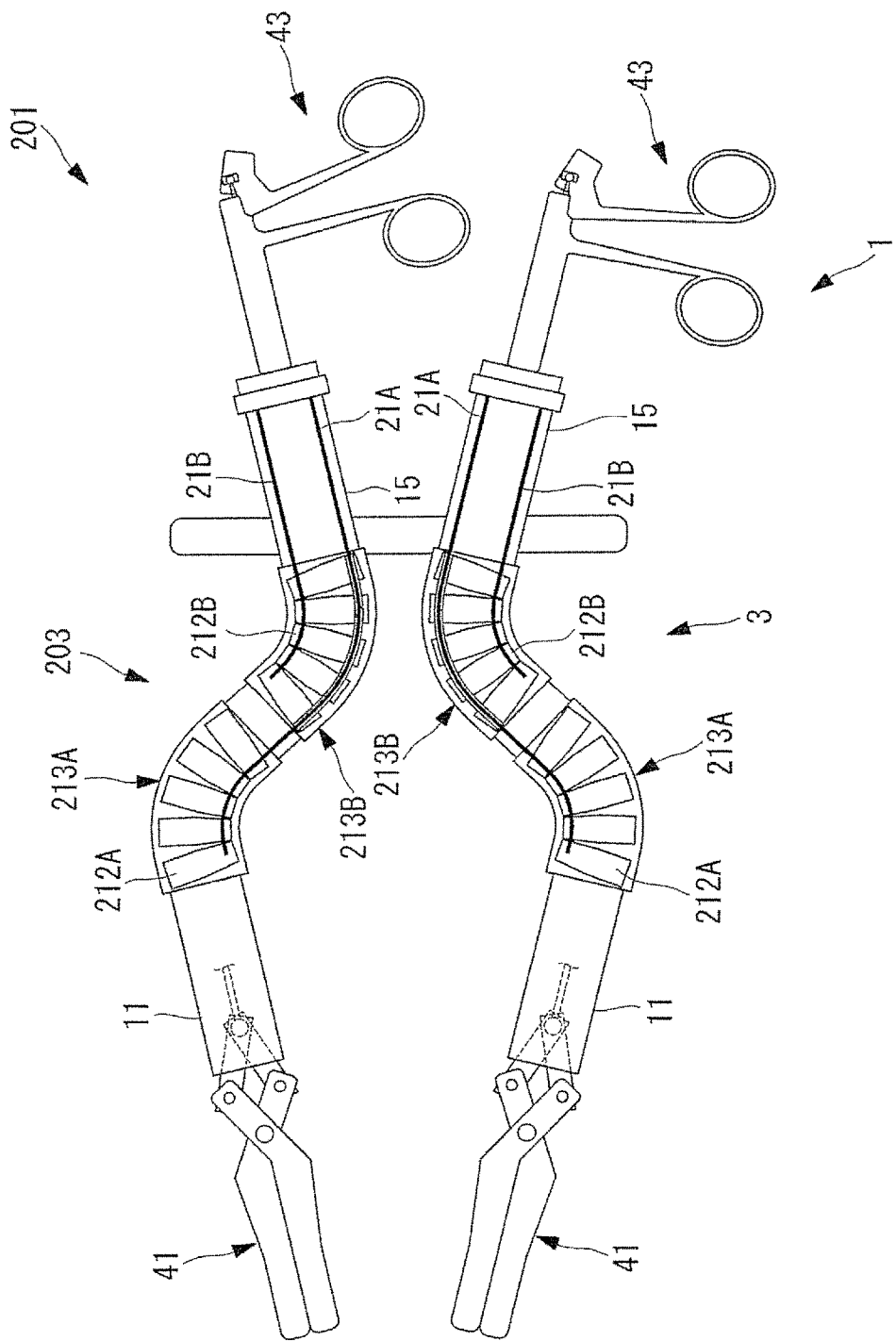
FIG. 10 shows that the mantle tube of FIG. 9 is bent in an S-bent state.

Here the interconnected structure-forming members 33 are spaced away from one another and arranged by the holding wire 31 in an S-shaped pattern in conformity with the bent shape of the bendable sites 213A and 213B. In this state, the adjoining interconnected structure-forming members 33 are pressed together by the pressing mechanism 34 such that they come close to each other to bring the connecting surfaces 33a and 33b into close contact with each other. In turn, this ensures that, as shown in FIG. 10, the interconnected state of the interconnected structure-forming members 33 bent in an S-shaped pattern in conformity with the bent shape of the bendable sites 213A and 213B is maintained by friction between the connecting surfaces 33a and 33b. It is thus possible to hold the bending angle of the bendable sites 213A and 213B of the bendable member 10 by virtue of the angle holding mechanism 30 and maintain the S-shaped bent state of the case 9. Note here that the angle holding mechanism 30 is left out of FIG. 10 for the sake of a clearer illustration of the bent state of the bendable member 10.

The mantle tube 203 and treatment tool 201 according to the embodiment of the invention as described above ensures that the S-shaped bent state of the case 9 is firmly held within the body cavity. It is thus possible to insert the mantle tube 203 into the body cavity while accommodating the body cavity's complicated form, allowing the forceps unit 41 of the flexible treatment tool 5 to gain easy access to the organ 4 of interest, etc.

While the bendable member 10 has two bendable sites 213A and 213B in the instant embodiment of the invention, it is to be noted that the bendable member 10 may have three or more bendable sites that are bendable in mutually different directions.

For instance, FIGS. 11A to 11D show an example where the bendable member includes three bendable sites. As shown, the bendable member 10 may comprise, in order from its front-end side, a front-end frame 11, a first frame 211A, a bendable site 213A, a second frame 211B, a bendable site 213B, a third frame 211C, a bendable site 213C, and a fourth frame 211D.

Figure 11B:
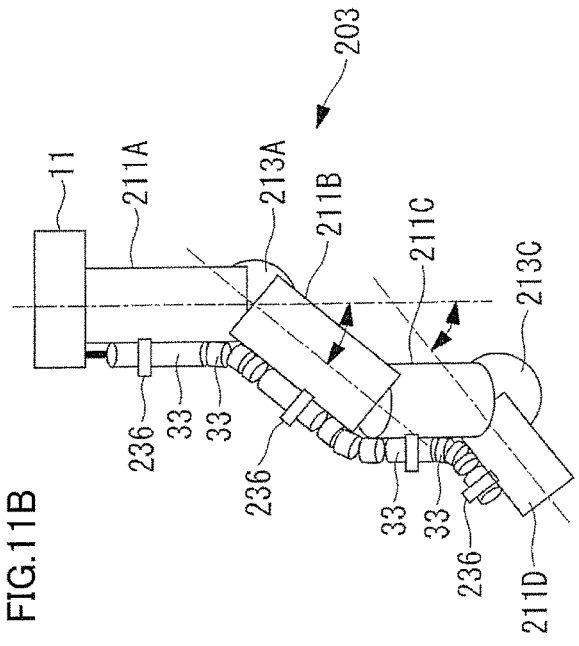
FIG. 11B shows schematically that the mantle tube according to a modification to the second embodiment of the invention is in a bent state.
Figure 11D:
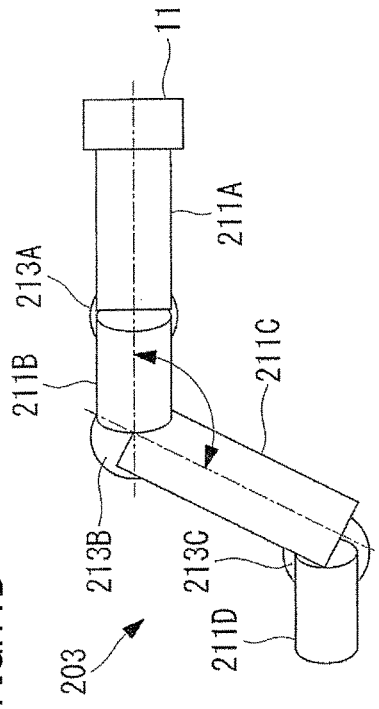
FIG. 11D is illustrative of the whole construction of a 3D endoscope system according to the second embodiment of the invention.
Figure 11A:
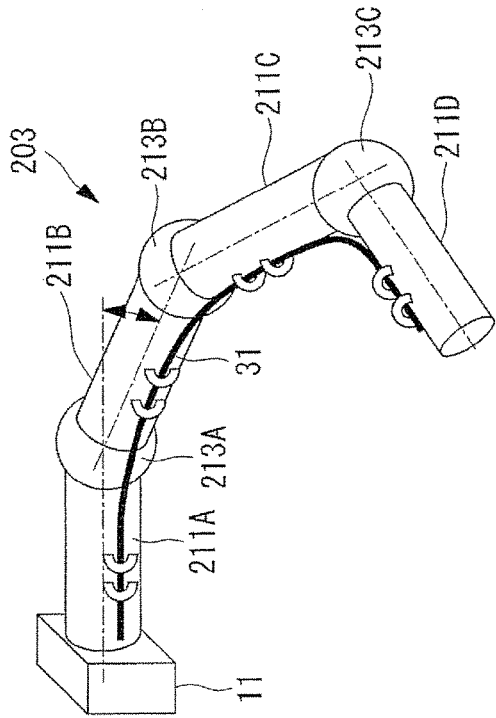
FIG. 11A is schematically illustrative of a mantle tube according to a modification to the second embodiment of the invention.
Figure 11C:
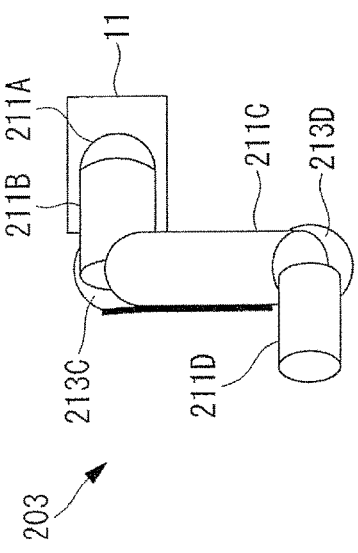
FIG. 11C shows schematically that the mantle tube according to a modification to the second embodiment of the invention is in other bent state.

In this case, as shown typically in FIG. 11B, an interconnected structure-forming member 33 having a long axial length may be located at positions corresponding to the first frame 211A, second frame 211B, third frame 211C and fourth frame 211D, and multiple interconnected structure-forming members 33, each having a short axial length, may be located at positions corresponding to the bendable sites 213A, 213B and 213C. For instance, a semi-circular curved holding member 236 or the like may be provided for each of the first frame 211A, second frame 211B, third frame 211C and fourth frame 211D for axial movement of the long interconnected structure-forming member 233.

In the embodiments and modifications as described above, the pressing mechanism 34 operates such that the gear 35 is rotated for movement of the pressing frame 37 thereby spacing the interconnected structure-forming members 33 away from one another or allowing them to come into contact with one another; however, it is to be understood that the invention is not limited thereto. For instance, the interconnected structure-forming members 33 may come into contact with each other by turning on electromagnetic force, and they may be spaced away from each other by turning off electromagnetic force.

Third Embodiment of the Invention

Figure 12:
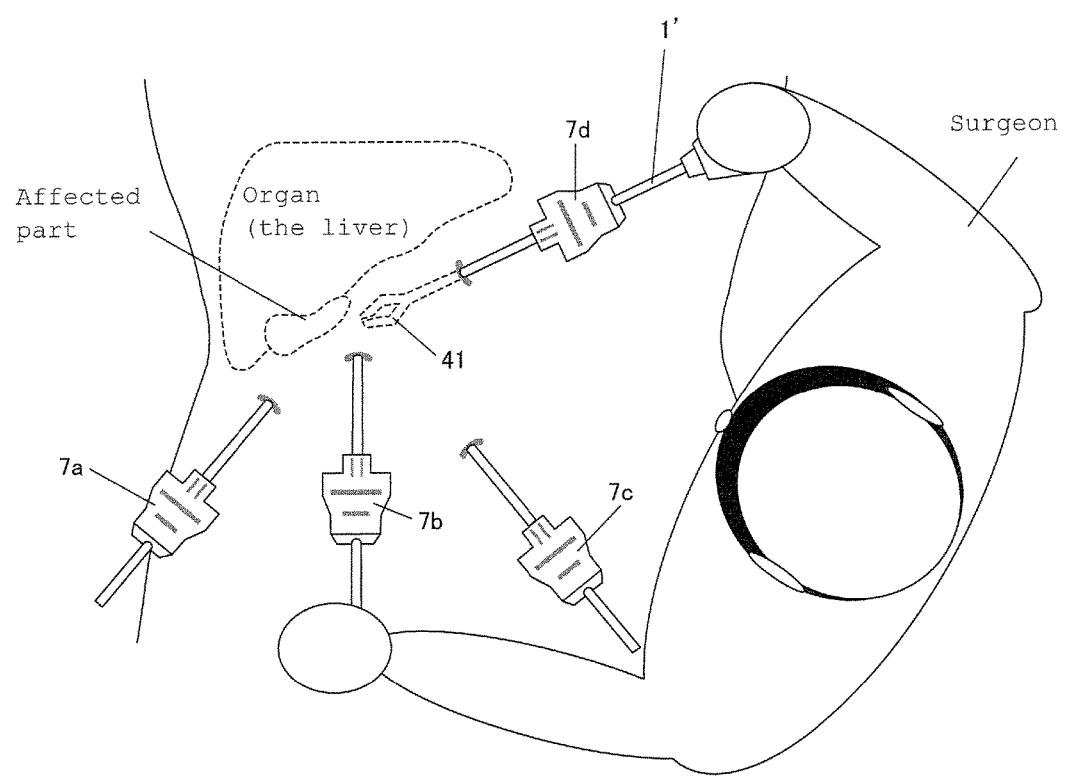
FIG. 12 is illustrative of how laparoscopic surgery using a treatment tool (i.e., forceps) is performed.

Reference will now be made to the third embodiment of the invention wherein the treatment tool of the invention is applied to forceps. FIG. 12 is illustrative of how laparoscopic surgery using forceps is carried out. In laparoscopic surgery, the abdomen or the like of a patient is opened up in multiple sites for insertion of various tools such as a camera, forceps and a (radio) knife, and the affected part is checked up and operated under observations of images taken by the camera. With this laparoscopic surgery, it is possible to relieve the patient of burdens because of a limited incision area.

In laparoscopic surgery, tubes called trocars (channels) 7a to 7d are put into a hole opened up in the body wall of the patient, and various treatment tools are inserted in the body cavity of the patient through the trocars 7a to 7d. FIG. 12 is illustrative of forceps 1' being inserted into the trocar 7d. A forceps unit 41 is provided at a front-end portion of the forceps 1' inserted into the body cavity of the patient through the trocar 7d, and a surgeon makes full use of the forceps 1' for opening or closing the forceps unit 41, operating on the affected part.

Thus far the forceps 1' was fixed in length. In order to move the forceps unit 41 of the forceps 1' to a proper position such as the affected part, it was necessary for the surgeon to bring the forceps 1' to hand. For this reason, there was a large change in the handle position of the forceps 1' in major operations such as total extirpation of the large bowel, which forced the surgeon to assume an unreasonable posture. Thus, prior art treatment tools had poor operability.

Figure 13B:
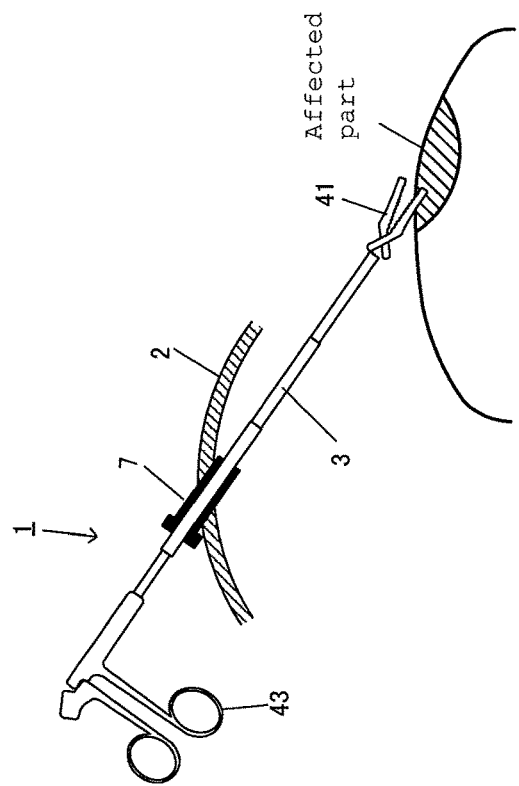
FIGS. 13A and 13B are illustrative of how an operation using the treatment tool according to the third embodiment of the invention is performed.
Figure 13A:
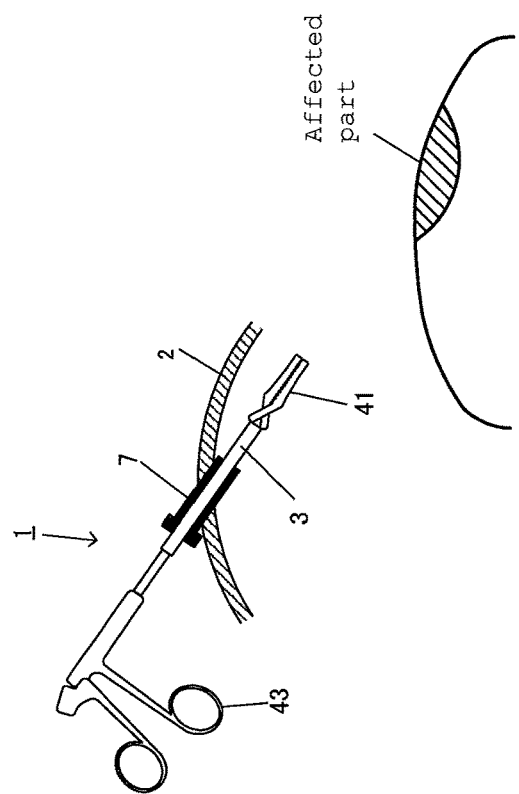

FIGS. 13A and 13B are illustrative of how operation is carried out using the treatment tool 1 according to the third embodiment of the invention. The treatment tool 1 according to the third embodiment of the invention is characterized by having an extendable construction for the purpose of improving the operability of the conventional treatment tool. In the present disclosure, the treatment tool 1 is explained taking forceps including a forceps unit 41 on an end effector as an example. Various embodiments including cameras, (radio) knives, etc. on the end effector may be used as the treatment tool 1.

FIG. 13A is illustrative of the treatment tool 1 inserted into the abdominal cavity through the trocar 7. Specifically, FIG. 13A shows that the forceps unit 41 is away from the affected part. With the treatment tool 1 according to the third embodiment of the invention, the forceps unit 41 may be moved by extension and contraction of the mantle tube 3 to a proper position such as the affected part. FIG. 13B is illustrative of the treatment tool 1 having the mantle tube 3 in an extended state. From a comparison with FIG. 13A, it is found that with a grip of the treatment tool 1, the forceps unit 41 moves to a proper position with no or little change in the position of the operating unit 43 where the forceps unit 41 is to be operated. Therefore, the surgeon who grips and operates the treatment tool 1 may move the end effector (the forceps unit 41 here) to a proper position with no or little change in the position of the operating unit 43, resulting in improvements in the operability of the treatment tool 1.

Third Embodiment of the Invention

Figure 14:
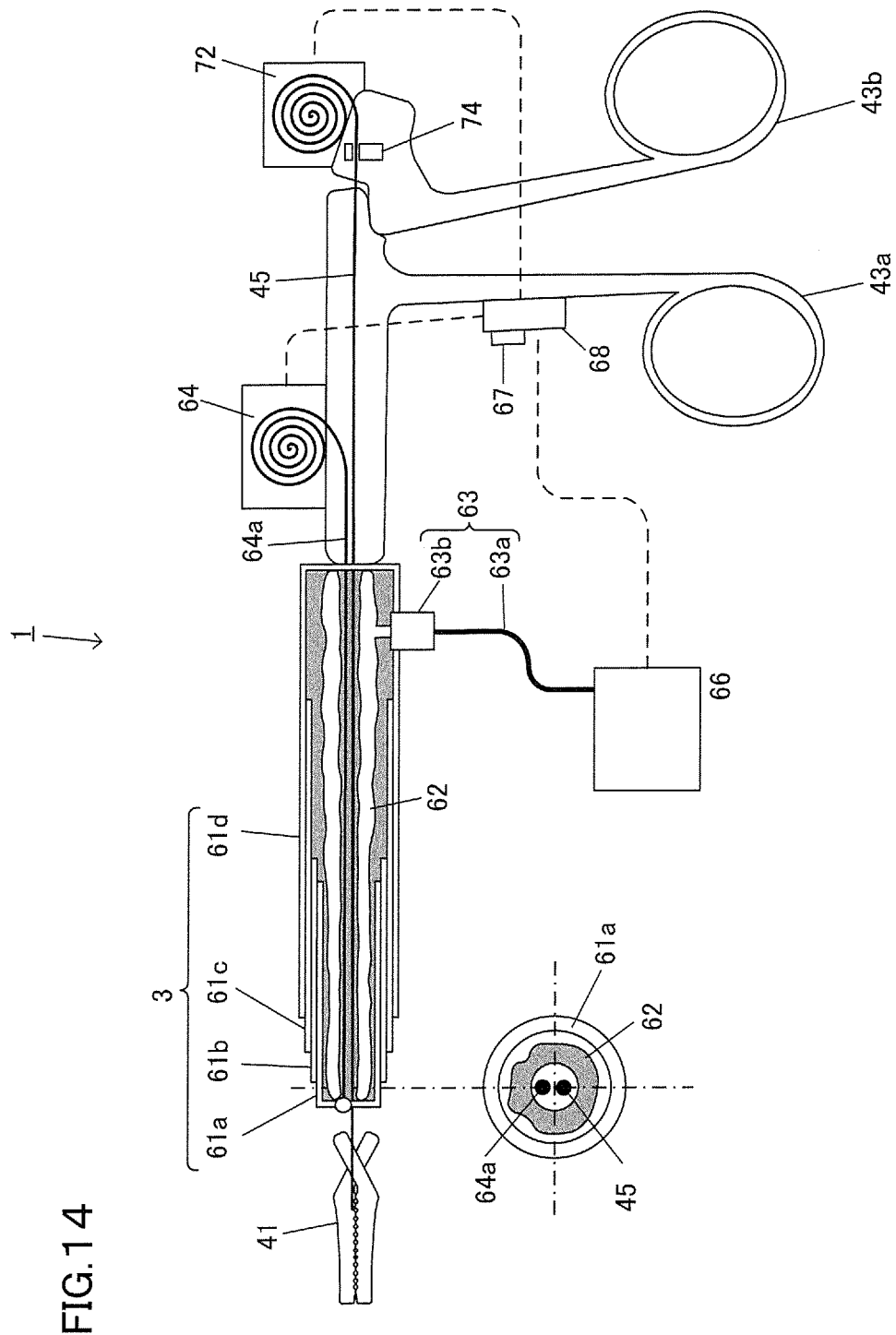
FIG. 14 is illustrative in construction of a treatment tool according to the third embodiment of the invention (upon contraction).

The construction or arrangement of this treatment tool 1 is explained typically with reference to the third embodiment of the invention. FIG. 14 shows the construction of the treatment tool 1 according to the third embodiment of the invention. Including the forceps unit 41 on the end effector, this treatment tool 1 is known as the so-called forceps for use on making an operation on the body cavity of the patient.

This treatment tool 1 is made up of a mantle tube 3, a forceps unit 41 operating as an end effector, a means for varying the amount of extension and contraction, an operating means, and a control means.

Figure 15:
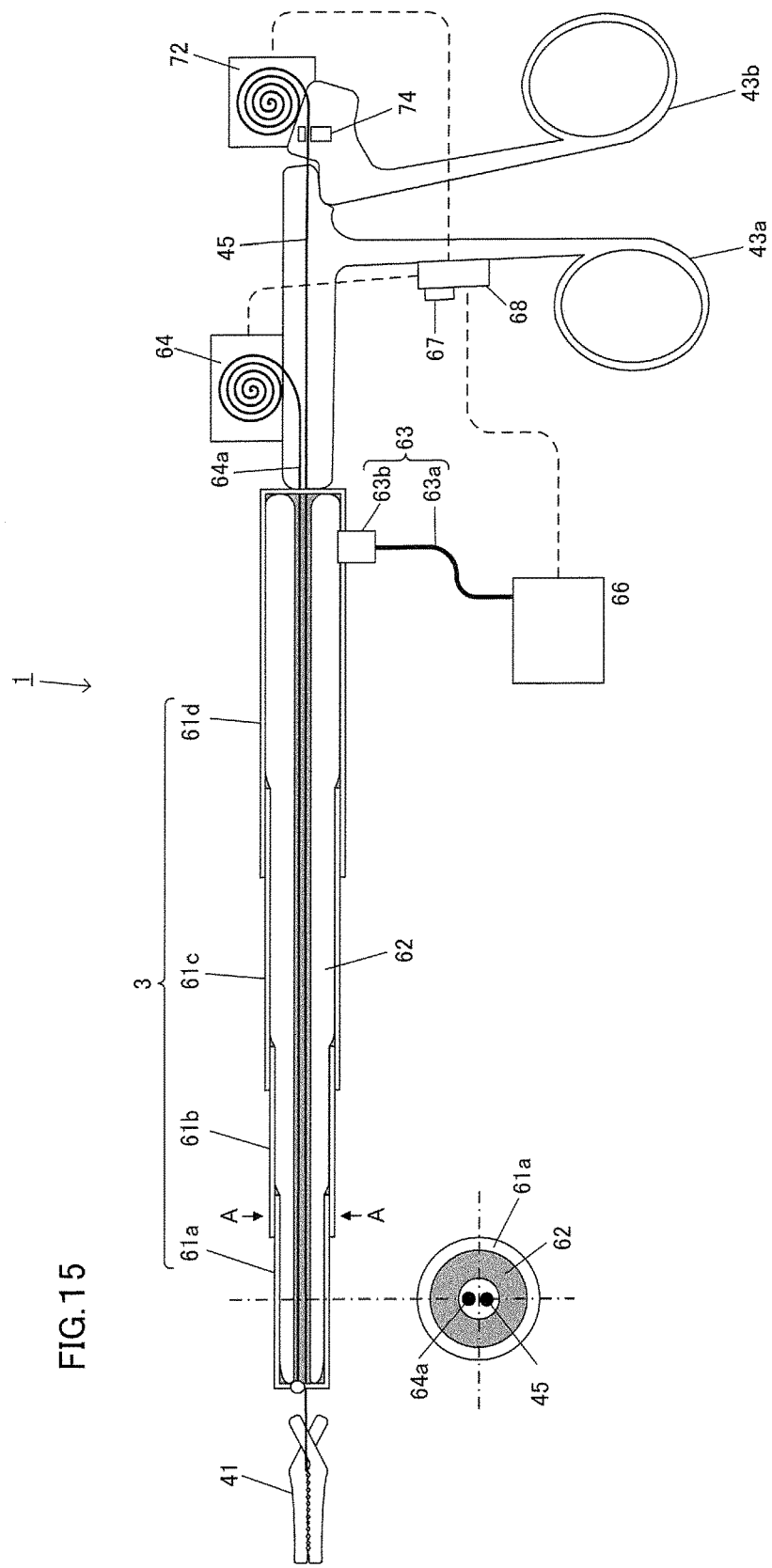
FIG. 15 is illustrative in construction of the treatment tool according to the third embodiment of the invention (upon extension).

The mantle tube 3 is made up of a plurality of unit sheath tubes 61*a* to 61*d*. Each unit sheath tube 61*a* to 61*d* has a diameter large enough to be received in an adjoining unit sheath tube, and the mantle tube 3 contracts as shown in FIG. 14 while it extends as shown in FIG. 15. The mantle tube 3 may be provided with various stopper mechanisms for the purpose of preventing the unit sheath tubes 61*a* to 61*d* from coming out.

The means for varying the amount of extension and contraction is provided to extend and contract the mantle tube 3 from within; in the third embodiment of the invention, it is made up of a pressure-receiving part 62, a pressure source 66, a pressure medium path 63, and an adjustment part 64 for adjusting a wire for limiting extension and contraction. The pressure-receiving part 62 is a member that is made expandable by a liquid, a gas or other pressure medium contained inside, and that may be formed of various materials such as rubber or films. This pressure-receiving part 62 is connected at its left front end to the unit sheath tube 61*a* and at its right front end to the unit sheath tube 61*d*. Such construction makes it possible to control the amount of extension and contraction by the amount of the pressure medium contained in the pressure-receiving part 62. At the lower left of FIG. 14, there is a sectional view of the unit sheath tube 61*a* presented. As shown, the pressure-receiving part 62 has an annular section, and may have an extension/contraction-limiting wire 64*a* and a transmission wire 45 received inside.

The pressure source 66 is a member that makes sure an inflow or outflow of the pressure medium into or from the pressure-receiving part 62 by way of the pressure medium path 63, and that controls the amount of inflow or outflow by a control unit 68. The pressure medium path 63 is made up of a connector 63*b* attached to the mantle tube 3 and a pipe 63*a* for providing a connection between the connector 63*b* and the pressure source 66. The connector 63*b* is connected to the pressure-receiving part 62 for an inflow or outflow of the pressure medium into or from the pressure-receiving part 62.

FIG. 14 shows that the amount of the pressure medium within the pressure-receiving part 62 is kept small. Thus, as the pressure medium within the pressure-receiving part 62 is reduced, it causes the unit sheath tubes 61*a* and 61*d* to be pulled nearer, or the mantle tube 3 to be contracted, by the extension/contraction-limiting wire adjusting part 64 connected to the unit sheath tube 61*a* for adjusting the wire for limiting extension and contraction. On the other hand, FIG. 15 shows a full inflow of the pressure medium into the pressure-receiving part 62. Expansion of the pressure-receiving part 62 causes the mantle tube 3 to receive force that expands it and be placed in its extended state. At the lower left of FIG. 15, there is a sectional view of the unit sheath tube 61*a* presented. The pressure-receiving part 62 is being expanded within the unit sheath tube 61*a*. The annular configuration of the pressure-receiving part 62, as described above, ensures that even when the pressure-receiving part 62 is expanding, there is a space provided for the extension-limiting wire 64*a* and transmission wire 45.

Figure 16:
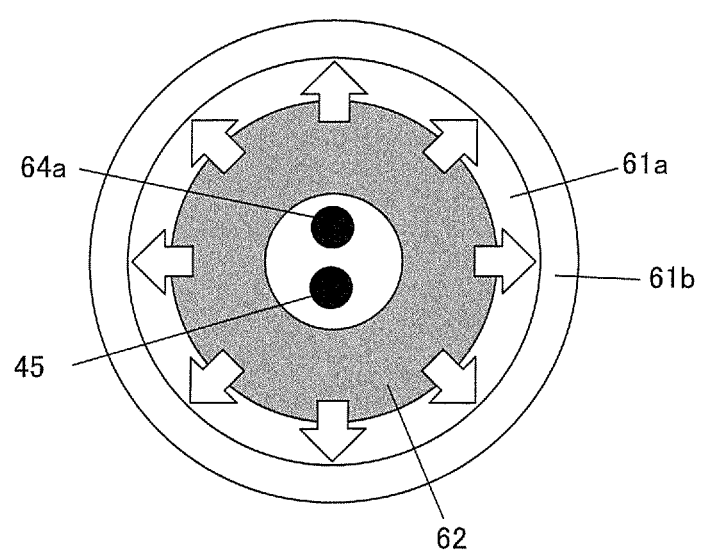
FIG. 16 is illustrative of the fixing mechanism for the treatment tool according to the third embodiment of the invention.

In the third embodiment of the invention, the pressure-receiving part 62 functions as a unit sheath tube-fixing means upon expansion. As depicted in FIG. 15, the respective unit sheath tubes 61*a* to 61*d* overlap one another at their junctions. FIG. 16 is illustrative in section of a junction (between line segments A-A) between the unit sheath tubes 61*a* and 61*b* in FIG. 15. At this junction, the expansion of the pressure-receiving part 62 acts on the internal surface of the unit sheath tube 61*a* to press the surface of the unit sheath tube 61*a* against the internal surface of the unit sheath tube 61*b*, resulting in a firm connection made between both the unit sheath tubes 61*a* and 61*b*.

The pressure-receiving part 62 acting as the unit sheath tube-fixing means also contributes to the straightness or rectilinearity of the overall mantle tube 3 (the straightness of the center axes of the unit sheath tubes 61*a* to 61*d*). The respective unit sheath tubes 61*a* to 61*d* should be extendable and contractible; so there must be some play provided at their junctions. However, provision of such a play would cause the center axes of the respective unit sheath tubes 61*a* to 61*d* to form an angle with one another, resulting in a loss of the straightness of the mantle tube 3. According to the third embodiment of the invention, the internal pressure from the pressure-receiving part 62 acts almost uniformly in every peripheral direction as shown in FIG. 16, making it possible to take hold of the straightness of the overall mantle tube 3 because any play, if any, between the respective unit sheath tubes 61*a* to 61*d* can be canceled out. It is thus possible for the surgeon to properly move the end effector such as the forceps unit 41 to the desired position during operation.

Only by the expansion and contraction of the pressure-receiving part 62, it is not possible to vary the length of the mantle tube 3 as desired. In other words, the mantle tube 3 is only set to the shortest length or the longest length. With the treatment tool 1 according to the third embodiment of the invention, the mantle tube 3 may be set to not only the shortest or the longest length but also to a length in between by provision of the extension/contraction-limiting wire adjustment part 64. The extension/contraction-limiting wire adjustment part 64 is fixedly provided on the unit sheath tube 61*d* side, and enables the extension-limiting wire 64*a* to be let out to a proper length by a driving unit such as a motor. The extension-limiting wire 64*a* is wound on one end side around the extension/contraction-limiting wire adjustment part 64 and connected on the other end side with the unit sheath tube 61*a*. The control unit 68 controls the extension/contraction-limiting wire adjustment part 64 to let out the extension-limiting wire 64*e* to a proper length corresponding to the amount of extension thereby limiting the length of the mantle tube 3.

Further, the treatment tool 1 according to the third embodiment of the invention may function as forceps; so it further includes an operating means for the forceps unit 41 provided at its front end. This operating means is made up of operating portions 43*a* and 43*b*, an operating wire adjustment part 72, a transmission wire 45, and a wire gripping part 74. The forceps unit 41 is designed such that its gripping part may be closed or opened by the transmission wire 45. The wire gripping part 74 enables the transmission wire 45 to be held open when the operating portions 43*a* and 43*b* are held open. With the operating portions 43*a* and 43*b* remaining closed, the wire gripping part 74 changes its position to pull the transmission wire 45 in the right direction while the transmission wire 45 remains gripped. Thus, closure of the operating portions 43*a* and 43*b* enables the forceps unit 41 to be held open.

The third embodiment of the invention further includes an operating wire adjustment part 72 that adjusts the amount of the transmission wire 45 to be let out to a proper length in association with length changes in the mantle tube 3. With this operating wire adjustment part 72, it is possible to wind or unwind the transmission wire 45 to a proper length by a driving unit such as a motor.

On the basis of operation of the extension/contraction switch 67, the control unit 68 controls the extension/contraction-limiting wire adjustment part 64, operating wire adjustment part 72 and pressure source 66, and controls the amount of the extension/contraction-limiting wire 64a and transmission wire 45 to be let out and the amount of the pressure medium in the pressure-receiving part 62 as well.

Figure 17:
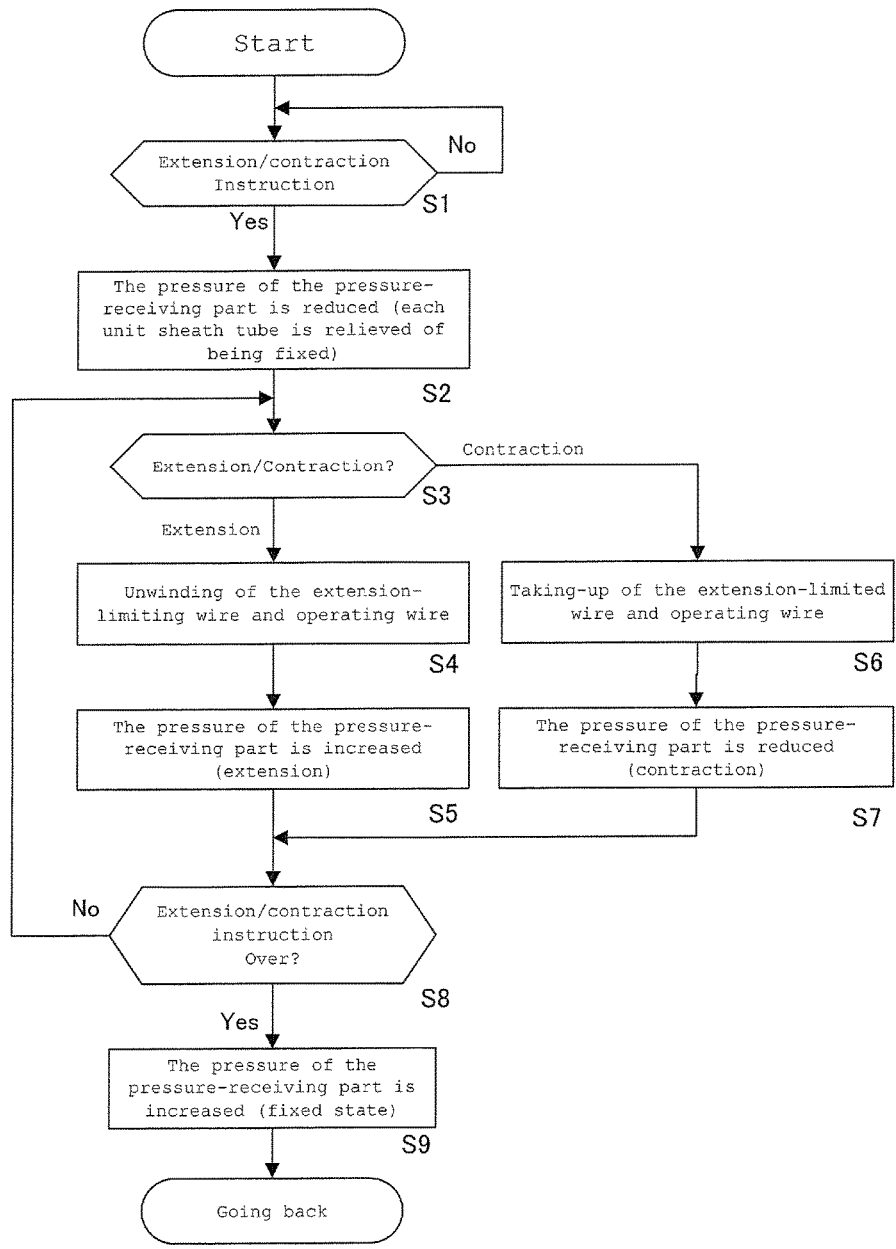
FIG. 17 is a flowchart illustrative of the extension/contraction operation of the treatment tool according to the third embodiment of the invention.

FIG. 17 is a flowchart indicative of extension and contraction taking place at the control unit 68 in the treatment tool 1.

An extension or contraction instruction may be entered by the surgeon into the extension/contraction switch 67. Upon entry of the extension or contraction instruction (S1: Yes), the pressure source 66 is actuated to reduce the pressure of the pressure medium in the pressure-receiving part 62, and the respective unit sheath tubes 61a to 61d are once released off from their fixed states (S2). Then, when the instruction to the extension/contraction switch 67 is an extension instruction, the extension/contraction-limiting wire adjustment part 64 and the operating wire adjustment part 72 are actuated to rewind the extension/contraction-limiting wire 64a and the transmission wire 45, respectively, to a proper length (S4). Here the pressure source 66 causes an inflow of the pressure medium into the pressure-receiving part 62 and the mantle tube 3 causes the extension/contraction-limiting wire 64a to be extended to the length limited by extension/contraction-limiting wire 64a (S5).

When the instruction to the extension/contraction switch 17 is a contraction instruction, on the other hand, the extension/contraction-limiting wire adjustment part 64 and the operating wire adjustment part 72 are actuated to take up the extension-limiting wire 64a and the transmission wire 45, respectively, to a proper length (S6). Here the pressure source 66 causes an outflow of the pressure medium from the pressure-receiving part 62, and the mantle tube 3 is contracted to the length limited by the extension/contraction-limiting wire 64a (S7).

On the basis of the extension and contraction instructions from the extension/contraction switch 67, the steps S3 to S7 are repeated to adjust the mantle tube 3 to a proper length. When the extension and contraction instructions exit as indicated by the fact that the extension/contraction switch 67 does not work for a given time and so on, the pressure source 66 is actuated to increase the pressure of the pressure medium in the pressure-receiving part 62 so that the respective unit sheath tubes 61 *a* to 61*d* pass from their open state into their closure state (S9).

While the treatment tool 1 according to the third embodiment of the invention has been explained, it is to be noted that it uses the pressure-receiving part 62 as the means for varying the amount of extension and contraction; the amount of the pressure medium in the pressure receiving part 62 is adjusted for adjustment of the length of the mantle tube 3. Further, the pressure-receiving part 62 functions as the fixing means for the junctions between the respective unit sheath tubes 61a to 61d to take firm hold of them, and contributes to improvements in the straightness of the mantle tube 3 as well. While this treatment tool 1 is specifically forceps using the forceps unit 41 at the end effector, it is to be appreciated that the end effector may be combined with various components such as cameras, (radio) knives, scissors, and retractors.

Fourth Embodiment of the Invention

Figure 18:
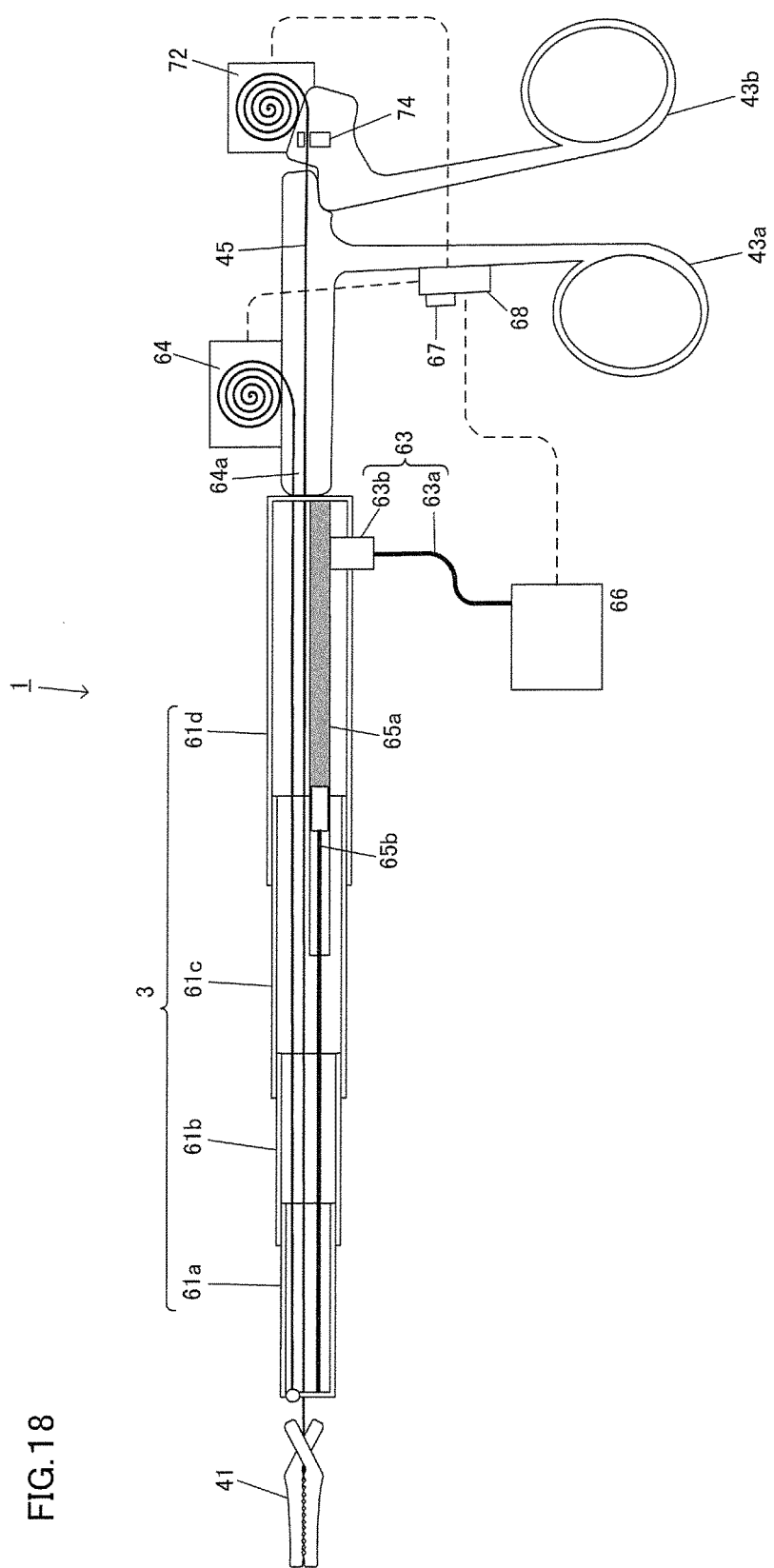
FIG. 18 is illustrative in construction of the treatment tool according to the fourth embodiment of the invention.

FIG. 18 is illustrative in construction of a specific treatment tool according to the fourth embodiment of the invention. As is the case with the third embodiment of the invention, the treatment tool 1 according to the fourth embodiment of the invention is forceps having the forceps unit 41 at an end effector. Although the third embodiment of the invention is designed such that the mantle tube 3 is extended or contracted by the expansion or contraction of the pressure-receiving part 62, it is to be understood that the fourth embodiment is different from the third embodiment in that the mantle tube 3 is extended or contracted on the basis of the amount of a pressure medium in a cylinder 65a.

The means for varying the amount of extension or contraction according to the fourth embodiment of the invention is made up of the cylinder 65a, a piston 65b, a pressure source 66, and a pressure medium path 63. The cylinder 65a is fixed to the unit sheath tube 61d, and the piston 65b is fixed to the unit sheath tube 61a. By adjustment of the amount of the pressure medium in the cylinder 65a, there is a variation taking place in the position of the piston 65b for adjustment of the amount of extension or contraction of the mantle tube 3.

On the basis of the operation of the extension/contraction switch 67, the control unit 68 causes an inflow or outflow of the pressure medium into or from the cylinder 65a through the pressure source 66. Upon an inflow of the pressure medium into the cylinder 65a, the mantle tube 3 extends, and upon an outflow of the pressure medium from the cylinder 65a, the mantle tube 3 contracts. As is the case with the third embodiment of the invention, the extension/contraction-limiting wire adjustment part 64 and the operating wire adjustment part 72 then work adjusting the extension/contraction-limiting wire 64a and the transmission wire 45, respectively, to a proper length depending on the amount of extension and contraction of the mantle tube 3. The open/close mechanism for the forceps unit 41 is the same as in the third embodiment.

Fifth Embodiment of the Invention

Figure 19:
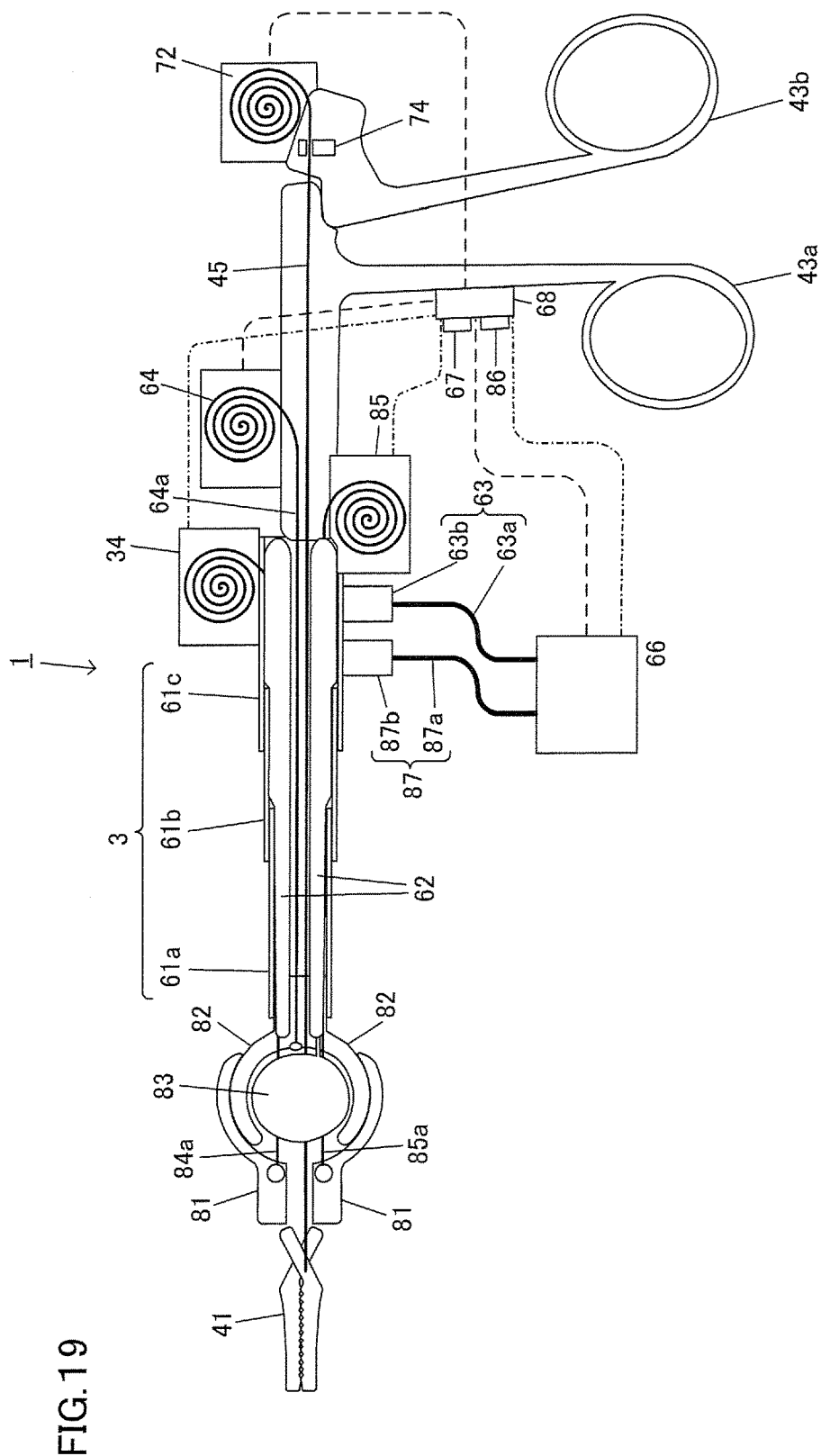
FIG. 19 is illustrative in construction of the treatment tool according to the fifth embodiment of the invention.

FIG. 19 is illustrative in construction of the treatment tool according to the fifth embodiment of the invention. The extension/contraction arrangement and movement of the mantle tube 3 according to the fifth embodiment, because of being the same as explained in the third embodiment, will not be explained any more. According to this fifth embodiment, the mantle tube 3 is provided at its front end with an angle adjustment means for an end effector (the forceps unit 41 here).

Figure 20:
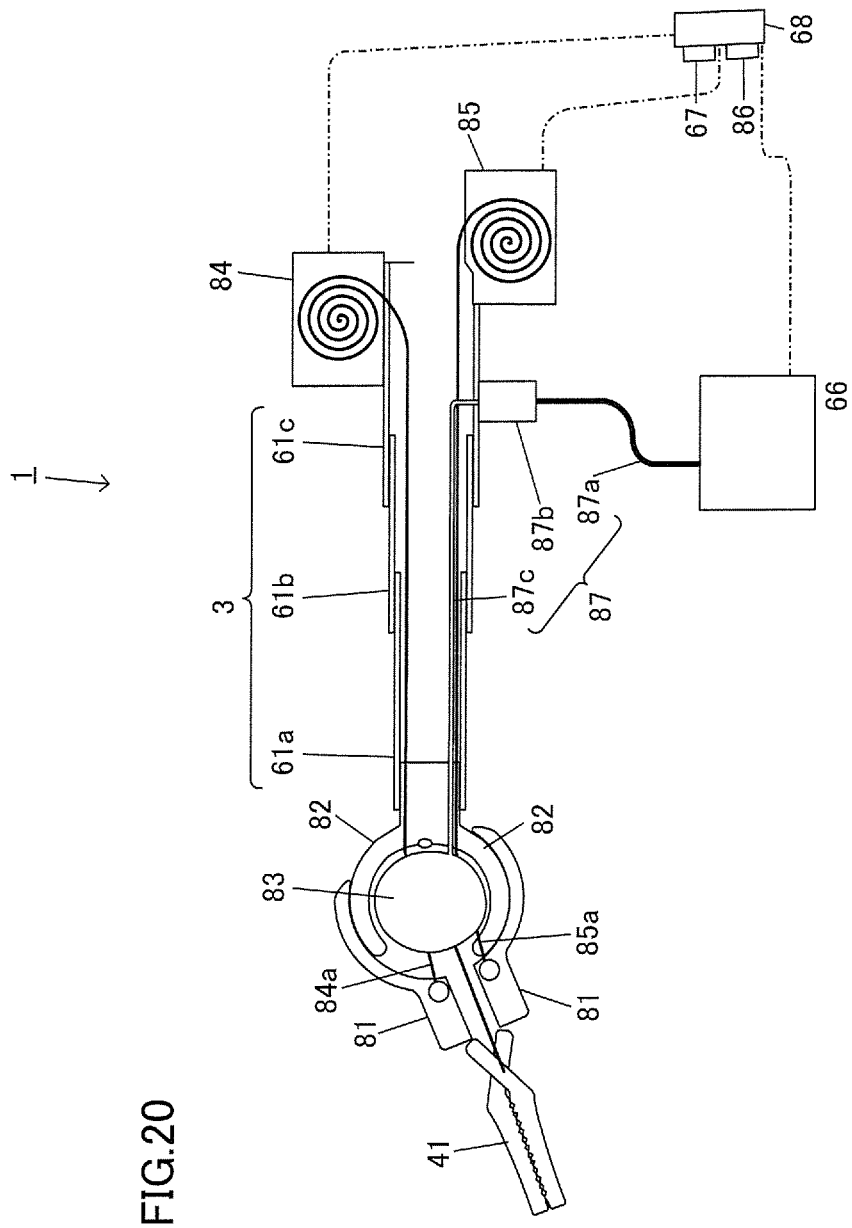
FIG. 20 is illustrative of the angle adjustment means for the treatment tool according to the fifth embodiment of the invention.

Comprising a spherical portion 82, a spherical surface-receiving portion 81, a second pressure receiver component 83, a first angle adjustment wire regulator component 84, a second angle adjustment wire regulator component 85 or the like, the angle adjustment means makes the forceps unit 41 vertically adjustable in terms of angle. The spherical portion 82 is a member that is fixed to the front end of the unit sheath tube 61a, and that has a spherical peripheral surface. The spherical surface-receiving portion 81 is provided at its front end with the forceps unit 41, and has an inside surface formed in conformity with the spherical surface portion 82. As the spherical surface-receiving 81 slides around and along the spherical surface portion 82, it enables the forceps unit 41 to be changed to any desired angle. FIG. 20 is illustrative of what state the angle adjustment means is placed in upon angle changes.

The second pressure receiver component 83 is provided in the junction between the spherical surface portion 82 and the spherical surface-receiving portion 81. As is the case with the pressure receiver 62 as explained with reference to the third embodiment of the invention, this second pressure receiver component 83 is formed of various materials such as rubber or films; the amount of the pressure medium inside is adjusted by the pressure source 66 through a second pressure medium path 87 comprising pipes 87a and 87c and a second connector 87b. Upon an inflow of a sufficient amount of the pressure medium into the second pressure receiver component 83, a certain fixing force acts on the junction between the spherical surface portion 82 and the spherical surface-receiving portion 81 from within, as in FIG. 16, so that the spherical surface-receiving portion 81 can be firmly fixed in place at the adjusted angle.

Adjustment of the angle of the spherical surface-receiving portion 81 is carried out by the first angle adjustment wire 84a and second angle adjustment wire 85a from the first angle adjustment wire adjustment part 84 and second angle adjustment wire adjustment part 85, respectively. The first 84 and second angle adjustment wire adjustment part 85 are capable of making adjustment of the amount of the respective wires 84a and 85a to be let out by a motor or the like. On the basis of an angle adjustment instruction from the angle adjustment switch 86, the control unit 68 makes adjustment of the amount of the first 84a and the second angle adjustment wire 85a to be let out, and makes adjustment of the angle of the forceps unit 41.

FIG. 20 is illustrative of the rewinding of the first angle adjustment wire 84a and the taking-up of the second angle adjustment wire 85a from the state of FIG. 19, with the forceps unit 41 facing downward. Upon angle adjustment, the pressure source 66 reduces the pressure of the pressure medium in the second pressure-receiving part 83 to such an extent that the spherical surface-receiving portion 81 rotates relative to the spherical surface portion 82. After the completion of angle adjustment by the first 84a and the second angle adjustment wire 85a, the pressure source 66 increases the pressure of the pressure medium in the second pressure-receiving part 83 via the second pressure medium path 87, allowing the spherical surface-receiving portion 81 to take firm hold of the junction defined on the spherical surface portion 82.

Upon extension and contraction of the mantle tube 3, the control unit 68 controls the first 84 and the second angle adjustment wire adjustment part 85 to control the first 84a and the second angle adjustment wire 85a to a proper length depending on the amount of extension and contraction of the mantle tube 3. The open/close mechanism for the forceps unit 41 is the same as in third embodiment of the invention.

Sixth Embodiment of the Invention

Figure 21:
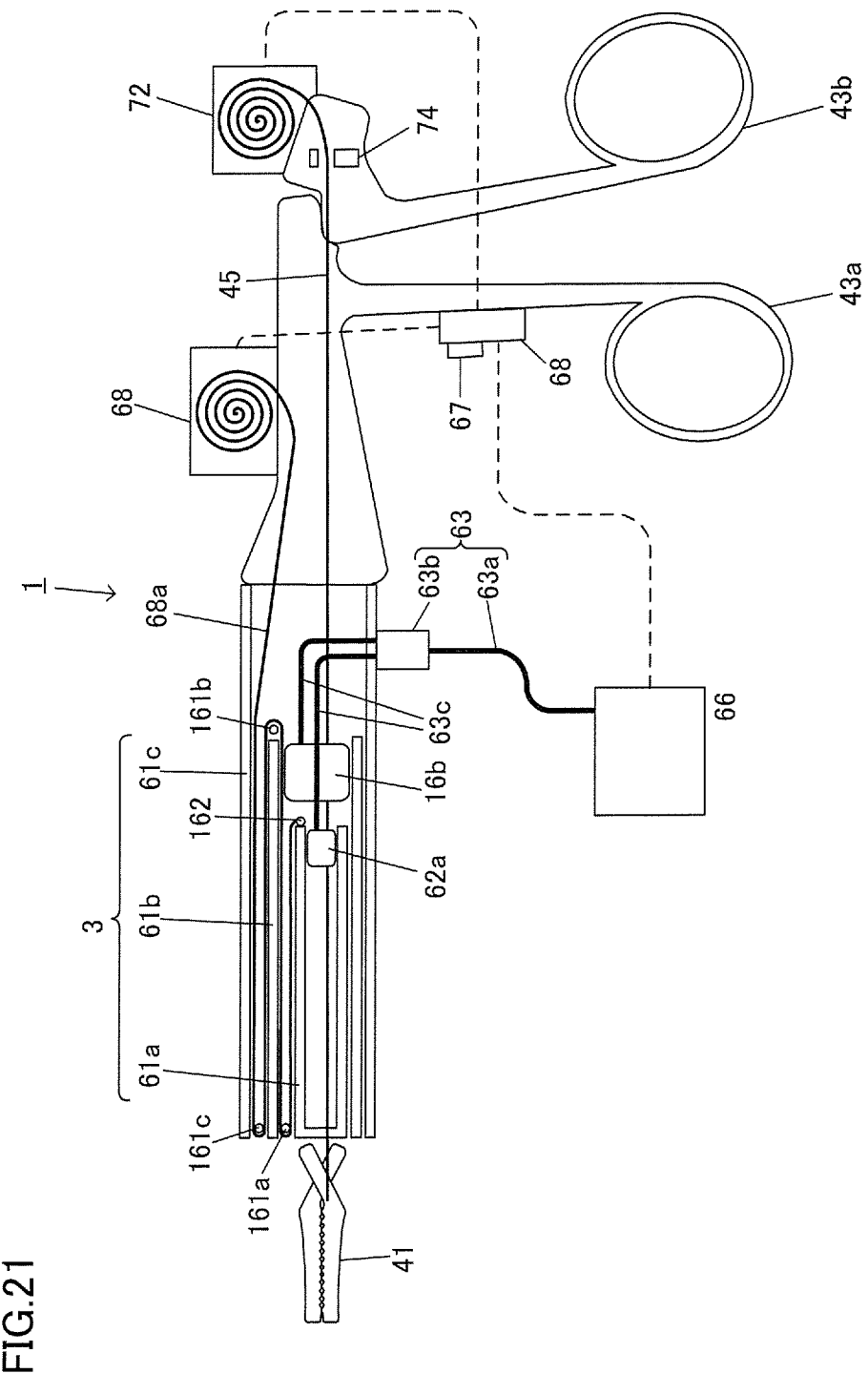
FIG. 21 is illustrative of the treatment tool according to the sixth embodiment of the invention (upon contraction).
Figure 22:
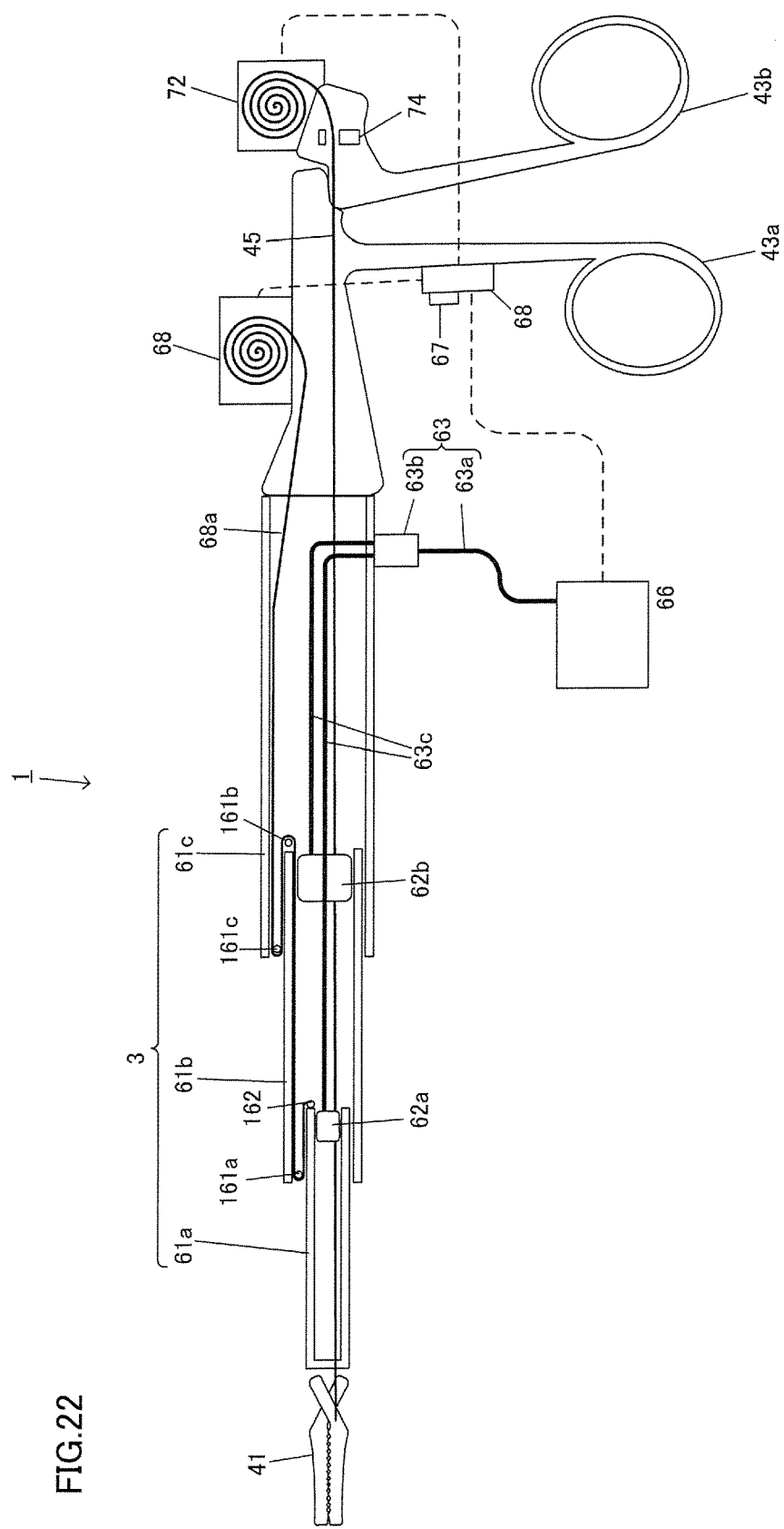
FIG. 22 is illustrative in construction of the treatment tool according to the sixth embodiment of the invention (upon extension).

FIGS. 21 and 22 are illustrative in construction of the treatment tool according to the sixth embodiment of the invention. FIG. 21 is illustrative of what state the treatment tool 1 contracts in, and FIG. 22 is illustrative of what state the treatment tool 1 extends in.

The treatment tool 1 according to the sixth embodiment of the invention is designed such that the extension and contraction of the mantle tube 3 is controlled by the amount of an extendable wire 68a to be let out by the extendable wire adjustment part 68. The unit sheath tube 61c is provided with a wire hook 161c, and the unit sheath tube 61b is provided with wire hooks 161a and 161b. The extendable wire 68a let out of the extendable wire adjustment part 68 is slidably wound around the wire hooks 161c, 161b and 161a in this order for fixation to the wire fixing part 162 of the unit sheath tube 61a. Therefore, by giving a pull to the extendable wire 68a at the extendable wire adjustment part 68, it is possible to extend the mantle tube 3. Note that the extendable wire 68a itself does not extend or contract in this embodiment.

Within the junction between the unit sheath tubes 61a and 61b and the junction between the unit sheath tubes 61b and 61c there are pressure-receiving parts 62a and 62b provided, respectively. These pressure-receiving parts 62a and 62b function as unit sheath tube-fixing means. Upon entry of an extension/contraction instruction into the extension/contraction switch 67, the control unit 68 operates such that the pressure of the pressure medium in the respective pressure-receiving parts 62a and 62b is reduced to relieve the mantle tube 3 of being fixed by the pressure-receiving parts 62a and 62b. After the amount of the extendable wire 68a to be let out is varied by the extendable wire-adjustment part 68 to adjust the mantle tube 3 to the desired length, the control unit 68 operates such that the pressure of the pressure medium in the respective pressure-receiving part 62a and 62b is increased to replace the mantle tube 3 in a fixed state. Thus, in the sixth embodiment of the invention, the pressure-receiving parts 62a and 62b are used only as the unit sheath tube-fixing means.

Seventh Embodiment of the Invention

Figure 23:
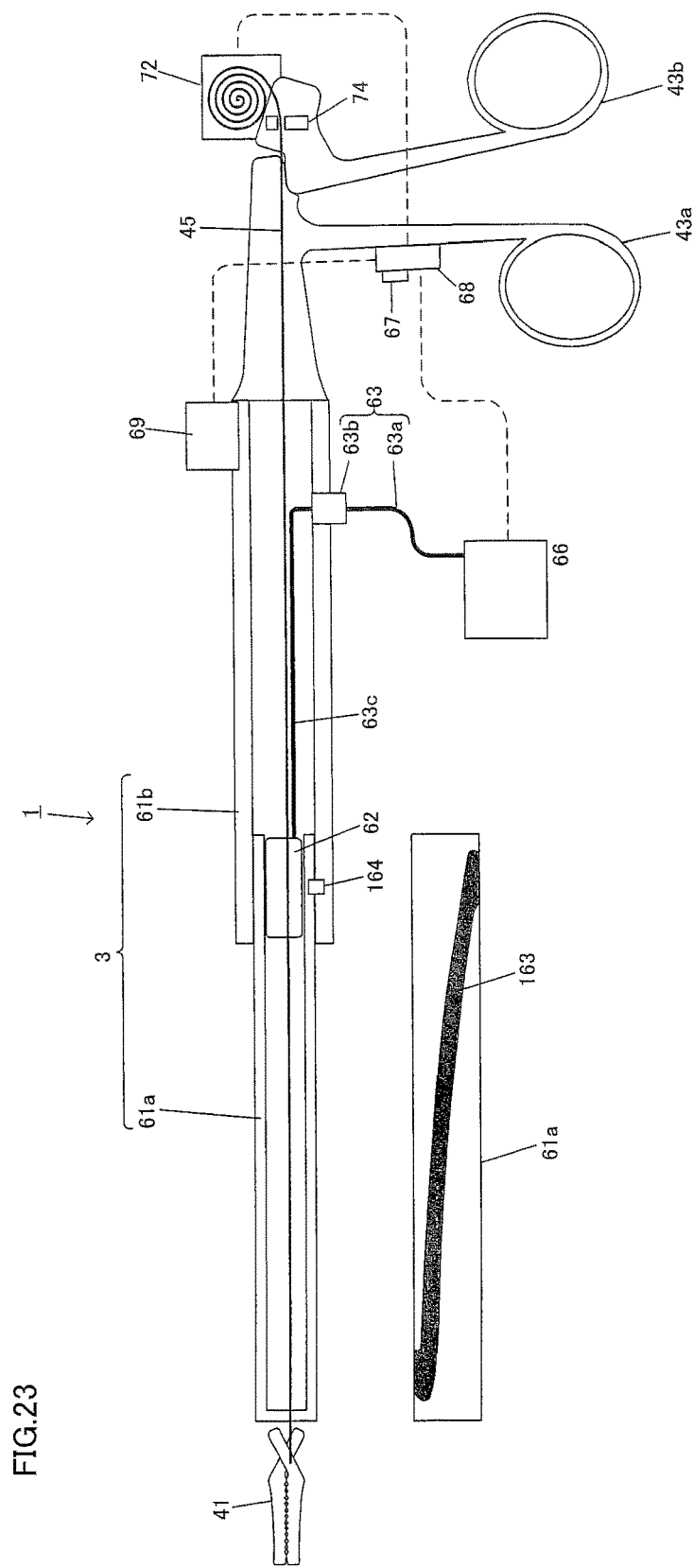
FIG. 23 is illustrative in construction of the treatment tool according to the seventh embodiment of the invention.

FIG. 23 is illustrative in construction of the treatment tool according to the seventh embodiment of the invention. In this seventh embodiment, a cam mechanism is used as the extension variable part for the mantle tube 3. At the lower left of FIG. 23, there is an illustration of the peripheral surface of the unit sheath tube 61a presented. This unit sheath tube 61a is provided on its peripheral surface with a cam 163 that is defined by a groove capable of engagement with a pin 164 provided on the internal surface of the unit sheath tube 61b. The unit sheath tube 61b is also capable of rotation relative to the unit sheath tube 61a by the driving force of a motor 69 for rotational movement. As the unit sheath tube 61b rotates relative to the unit sheath tube 61a, it causes the pin 164 in the unit sheath tube 61b to move forward or backward within the cam 163, letting the unit sheath tube 61a move into or out of the unit sheath tube 61b.

At the junction between the unit sheath tubes 61a and 61b there is a pressure-receiving part 62 provided. This pressure-receiving part 62 functions as a unit sheath tube-fixing means. Upon entry of an extension/contraction instruction into the extension/contraction switch 67, the control unit 68 operates on the pressure source 66 such that the pressure of the pressure medium in the respective pressure-receiving parts 62 is reduced to relieve the mantle tube 3 of being fixed by the pressure-receiving part 62. As the unit sheath tube 61b is rotated by the motor 69 for rotational movement, it causes the mantle tube 3 to be adjusted to the desired length. Then, the control unit 68 operates on the pressure source 66 such that the pressure of the pressure medium in the pressure-receiving part 62 is increased to place the mantle tube 3 in a fixed state. As is the case with the sixth embodiment, the pressure-receiving part 62 is used only as the unit sheath tube-fixing means.

Figure 24:
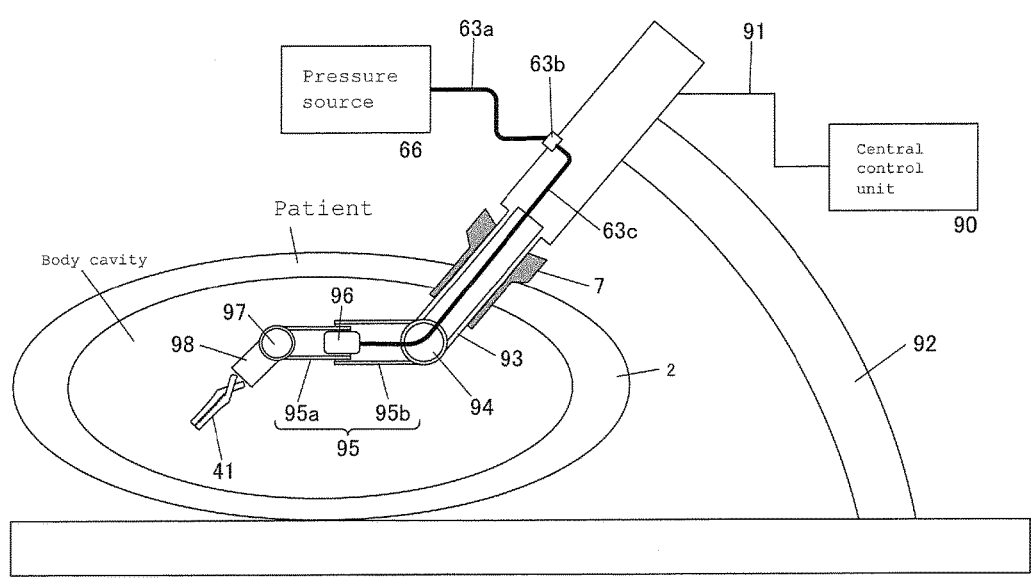
FIG. 24 is illustrative in construction of the treatment tool according to third embodiment of the invention as applied to a surgical manipulator.

The extension/contraction operation of some treatment tools according to the $3^{rd}$ to $7^{th}$ embodiments of the invention has been explained. While the treatment tools explained with reference to the 3$^{rd}$ to 7$^{th}$ embodiments have been shown as manually handled by the surgeon, it is to be appreciated that they may be applied to (or mounted on) a surgical assistant manipulator. FIG. 24 is illustrative in construction of the treatment tools according to the 3$^{rd}$ to 7$^{th}$ embodiments applied to a surgical assistant manipulator.

This surgical assistant manipulator is an apparatus or device that is capable of surgical operation and observation of the body cavity of a subject by remote control, and that is in a form supported by a support arm 92. A position on the support arm 92 may also be remote controlled. The surgical assistant manipulator according to this embodiment comprises a first arm 93, a second arm 95, a third arm 98, and a forceps unit 41. A first joint 94 makes a connection between the first 93 and the second arm 95, and a second joint 97 provides a connection between the second 95 and the third arm 98. A central control unit 90 operates on the adjustment of angle of each joint position such that the forceps unit 41 may be moved to a proper position.

The surgical assistant manipulators according to the 3$^{rd}$ to 7$^{th}$ embodiments of the invention each comprises the extension/contraction function of the treatment tool 1 explained with reference to the seventh embodiment, which is applied to the second arm 95. A motor for rotational movement (not shown) is actuated to relatively rotate the unit sheath tubes 95a and 95b of the second arm 95, making the second arm 95 extendable by a cam mechanism. At the junction between the unit sheath tubes 95a and 95b, there is a pressure-receiving part 96 located. This pressure-receiving part 96 operates such that the amount of a pressure medium inside may be adjusted by a pressure source 66 to selectively place the unit sheath tube 95a and 95b in an extendable or fixed state. The central control unit 90 operates such that the amount of rotation by the motor for rotational movement and the amount of the pressure medium in the pressure-receiving part 96, fed from the pressure source 66, may be adjusted to adjust the second arm 95 to a proper length.

Thus, when the treatment tools according to the 3$^{rd}$ to 7$^{th}$ embodiments of the invention are applied to a surgical assistant manipulator, the arms are extendable or contractible within the body cavity; so the range of manipulation of a portion of the manipulator outside of the body may be kept small. Especially when multiple manipulators are used, mutual interferences between them may be held back, contributing to improved operability. While the 3$^{rd}$ to 7$^{th}$ embodiments of the invention have been explained taking wires as an example of wire members, it is to be noted that cables may be used instead, or rods may be used if they are extendable or contractible.

While some embodiments of the invention have been described in details with reference to the accompanying drawings, it is to be appreciated that the invention is not specifically limited to them, and design changes may be carried out without departing from the purport of the invention. The invention is not limited to the embodiments or modifications that are illustrated and described; by way of example alone, such embodiments and modifications may be combined together in various forms.

While the respective embodiments of the invention have been explained taking the flexible treatment tool 5 having the forceps unit 41 as an example of medical equipment, it is to be noted that for instance, scissors, radio knives, retractors or similar tools having a surgical member for performing an operation on the site of interest may be adopted as the medical equipment.

The mantle tube and treatment tool according to the invention can be firmly held in the desired curved shape.

1, 201—Treatment tool
3, 203—Mantle tube
9—Case (cylindrical Member)
10—Bendable member
11—Front-end frame (fixed site)
13—Coil spring (bendable site)
15—Rear-end frame (fixed site)
20—Angle adjustment member
30—Angle holding mechanism
31—Holding wire (wire member)
33—Interconnected structure-forming member
34—Pressing mechanism (pressing member)
33a, 33b—Connecting surfaces
41—Forceps unit (treatment tool)
43—Operating unit
45—Transmission wire (transmission unit)
61—Extendable sheath tube
161a to 161c—Wire hook
162—Wire fixing part
163—Cam
164—Pin
61a to 61d—Unit sheath tube
62—(First) pressure-receiving part
63—(First) pressure medium path
63a, 63c—Pipe
63b—Connector
64—Extension/contraction-limiting wire adjusting part
64a—Extension/contraction-limiting wire
65a—Cylinder
65b—Piston
66—Pressure source
67—Extension/contraction switch
69—Motor for rotational movement
72—Operating-wire adjustment part
73a, 73b—Gripping member
74—Wire gripping part
81—Spherical surface-receiving portion
82—Spherical surface portion
83—Second pressure-receiving part
84—First angle adjustment wire adjusting part
84a—First angle adjustment wire
85—Second angle adjustment wire adjusting part
85a—Second angle adjustment wire
86—Angle adjustment switch
87—Second pressure medium path
87a—Pipe
87b—Connector
87c—Pipe
90—Central control unit
91—Control line
92—Support arm
93—First arm
94—First joint
95—Second arm
95a, 95b—Unit sheath
96—Pressure-receiving part
97—Second joint
98—Third arm
113—Link (bendable site)
132—Resilient member
133a, 133b—Connecting portions
213—Bendable site

What is claimed is:

1. A mantle tube, comprising:

a bendable member formed to be received in an elongate, annular, cylindrical member, the bendable member including two fixed sites that are fixed to the cylindrical member and a bendable site that is interposed between the fixed sites and bendable in a direction intersecting a longitudinal direction thereof, so that the cylindrical member is bent following the bendable site in the direction intersecting a longitudinal direction thereof, an angle adjustment member capable of adjusting a bending angle of the bendable site, and an angle holding mechanism capable of holding the bendable site bent by the angle adjustment member at any desired bending angle;

wherein the angle holding mechanism comprises:

a flexible wire member extending along the bendable member, the flexible wire member being fixed at one end to a front-end side fixed site of the bendable member, a plurality of interconnected structure-forming members arranged along the wire member and capable of coming into contact with one another, the plurality of interconnected structure-forming members being spaced away from one another in an arrangement direction, and a pressing member for causing the interconnected structure-forming members to be guided by the wire member so that the interconnected structure-forming members are pressed together along the arrangement direction so as to come close to one another, wherein the plurality of interconnected structure-forming members are pressed together by the pressing member in the arrangement direction whereby an interconnected state thereof bent following a bent shape of the bendable member is maintained by friction.

2. The mantle tube as recited in claim 1, wherein:

the bendable member includes at least two the bendable sites that are capable of bending in mutually different directions, and the angle adjustment member is capable of angle adjustment for each of the bendable sites.

3. The mantle tube as recited in any one of claim 1, wherein:

the wire member is inserted through all of the interconnected structure-forming members in the arrangement direction and fixed to the interconnected structure-forming member at a foremost end, and the pressing member applies a press to the interconnected structure-forming member at a rearmost end, the press being toward the foremost end of the arrangement direction.

4. The mantle tube as recited in any one of claim 1, wherein:

the interconnected structure-forming member includes a spherical connecting surface having a mutual correlation to an adjoining other interconnected structure-forming member.

5. The mantle tube as recited in any one of claim 1, wherein:

the interconnected structure-forming member includes a connecting portion having a mutual correlation to an adjoining other interconnected structure-forming member, and those connecting portions are connected together to impose limitation on a bending of the bendable member in a direction intersecting a bending direction of the bendable member.

6. The mantle tube as recited in any one of claim 1, wherein:

the angle holding mechanism includes a resilient member interposed between adjoining ones of the interconnected structure-forming members, the resilient member being capable of absorbing force of contact of the interconnected structure-forming members with each other.

7. The mantle tube as recited in any one of claim 1, wherein:

the bendable member includes an insertion path through which a medical device is insertable, and the angle holding mechanism is located outside of the insertion path of the bendable member.

* * * * *